United States Patent [19]

Ishikawa

[11] Patent Number: 5,236,849

[45] Date of Patent: Aug. 17, 1993

[54] METHOD OF HIGH SENSITIVITY IMMUNOASSAY

[76] Inventor: Eiji Ishikawa, 24-1, Ohtsukadainishi 3-chome, Miyazaki-shi, Miyazaki, Japan

[21] Appl. No.: 707,217

[22] Filed: May 24, 1991

Related U.S. Application Data

[63] Continuation of Ser. No. 227,820, Aug. 3, 1988, abandoned.

[30] Foreign Application Priority Data

| Aug. 11, 1987 | [JP] | Japan | 62-199149 |
| Apr. 5, 1988 | [JP] | Japan | 63-82349 |
| Apr. 5, 1988 | [JP] | Japan | 63-82350 |

[51] Int. Cl.$^5$ ........................... G01N 33/541
[52] U.S. Cl. ..................... 436/540; 436/512; 436/513; 436/518; 436/523; 436/524; 436/528; 436/532; 436/536; 436/538; 436/531
[58] Field of Search ............... 435/7.92, 7.9; 436/518, 436/531, 532, 8, 512, 513, 523, 524, 528, 536, 538, 540

[56] References Cited

U.S. PATENT DOCUMENTS

| 4,434,227 | 2/1984 | Unger | 436/509 |
| 4,486,530 | 12/1984 | David et al. | 436/548 |
| 4,670,383 | 6/1987 | Baier et al. | 435/7.93 |
| 4,711,839 | 12/1987 | Singhal | 436/506 |
| 4,945,042 | 7/1990 | Geiger | 435/7 |

FOREIGN PATENT DOCUMENTS

| 0174652 | 3/1985 | European Pat. Off. . |
| 0201339 | 11/1986 | European Pat. Off. . |
| 280211 | 2/1987 | European Pat. Off. . |
| 0236606 | 9/1987 | European Pat. Off. . |
| 218189 | 1/1985 | German Democratic Rep. . |
| 2029011 | 3/1980 | United Kingdom . |
| 2084317 | 4/1982 | United Kingdom . |

OTHER PUBLICATIONS

Chieregatti et al., An Immunoenzymometric Method Employing a 2nd Antibody . . . pp. 175–183, Monoclonol Antibodies & Dev'ts in Immunoassay, Albertini and Ekins, Eds, (1981).
Butler, Antibody–Antigen and Antibody–Hapten Reactions, pp. 6–45, (chapter 2) Enzyme Immunoassay, Maggio, Edition, 1987.
*Biochemical and Biophysical Research Communications,* vol. 147, No. 2, 644 to 649, Sep. 1987.
*Analytical Letters,* vol. 21, No. 6, pp. 1019 to 1031, 1988.
*Analytical Letters,* vol. 21, No. 7, pp. 1141 to 1154, 1988.
Kohno, *J. Biochem.,* vol. 100, 1247–1251, 1986.
Endo, "Handbook of Bio Separation Technology", Science Forum, Affinity Chromatography, pp. 150–163, 1988.
Sada, Biobech. & Bioeng., 21:341, 1979.
Hansen, Proc. Natl. Acad. Sci. USA, 79:2788, 1982.

*Primary Examiner*—Sam Rosen
*Attorney, Agent, or Firm*—Jacobson, Price, Holman & Stern

[57] ABSTRACT

A method of high sensitivity immunoassay characterized by inclusion of processes (A), (B), (C) and (D) described below.

Process (A): A process of binding of a solid carrier and a complex comprising the specific antibody or antigenic substance to be assayed in the test solution and one or more active components.

Process (B): A process of dissociating said complex from the solid carrier.

Process (C): A process of binding this complex to another solid carrier.

Process (D): A process of assay for the complex on the solid carrier mentioned in the description of process (C) above.

Permitting rapid, high sensitive immunoassay irrespective of whether the subject of assay is an antibody or an antigen, the method of the present invention is very useful for quick diagnosis of various diseases.

22 Claims, 8 Drawing Sheets

FIG_1

FIG_2

FIG_3

FIG_4

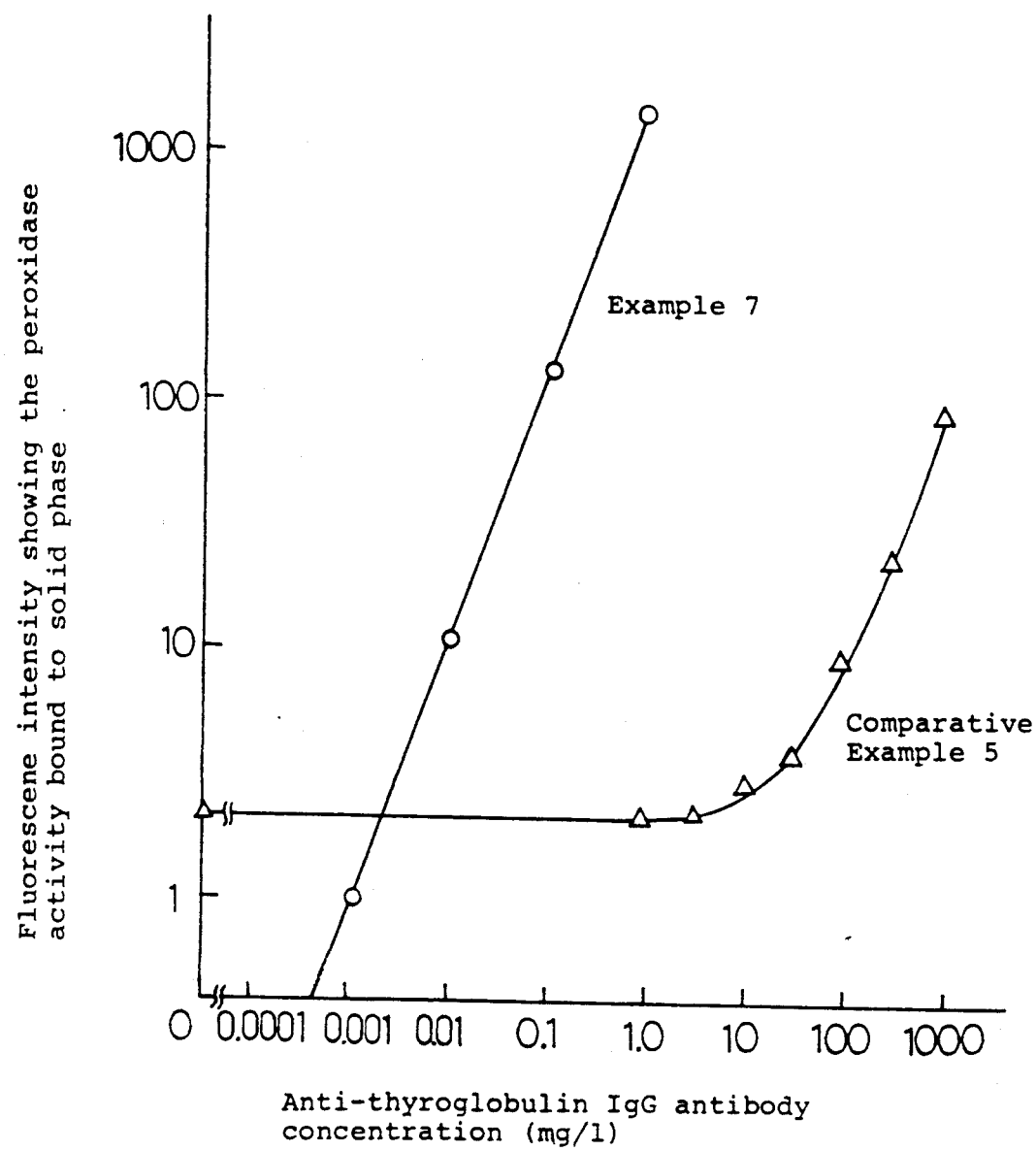
FIG_6

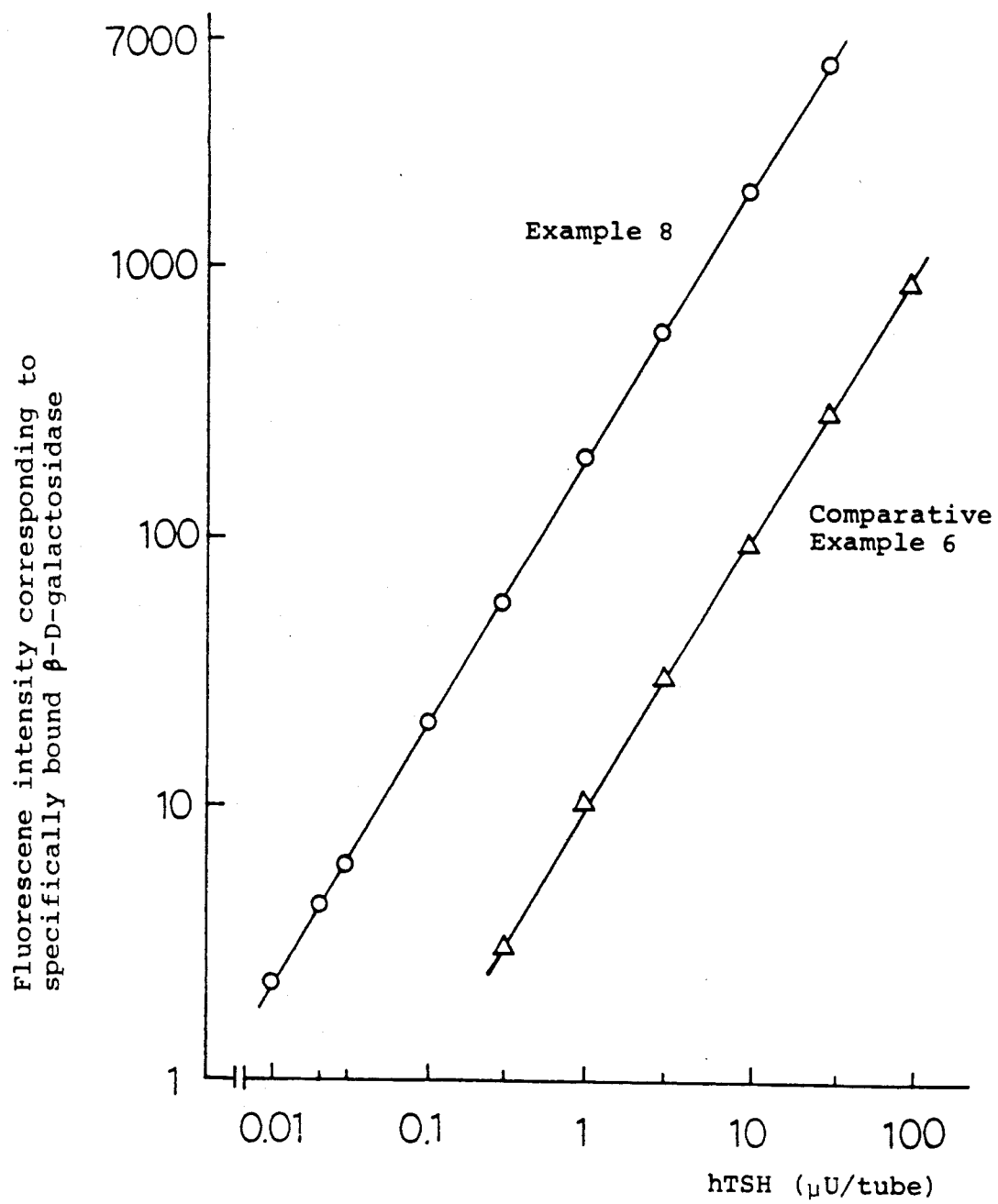
FIG_7

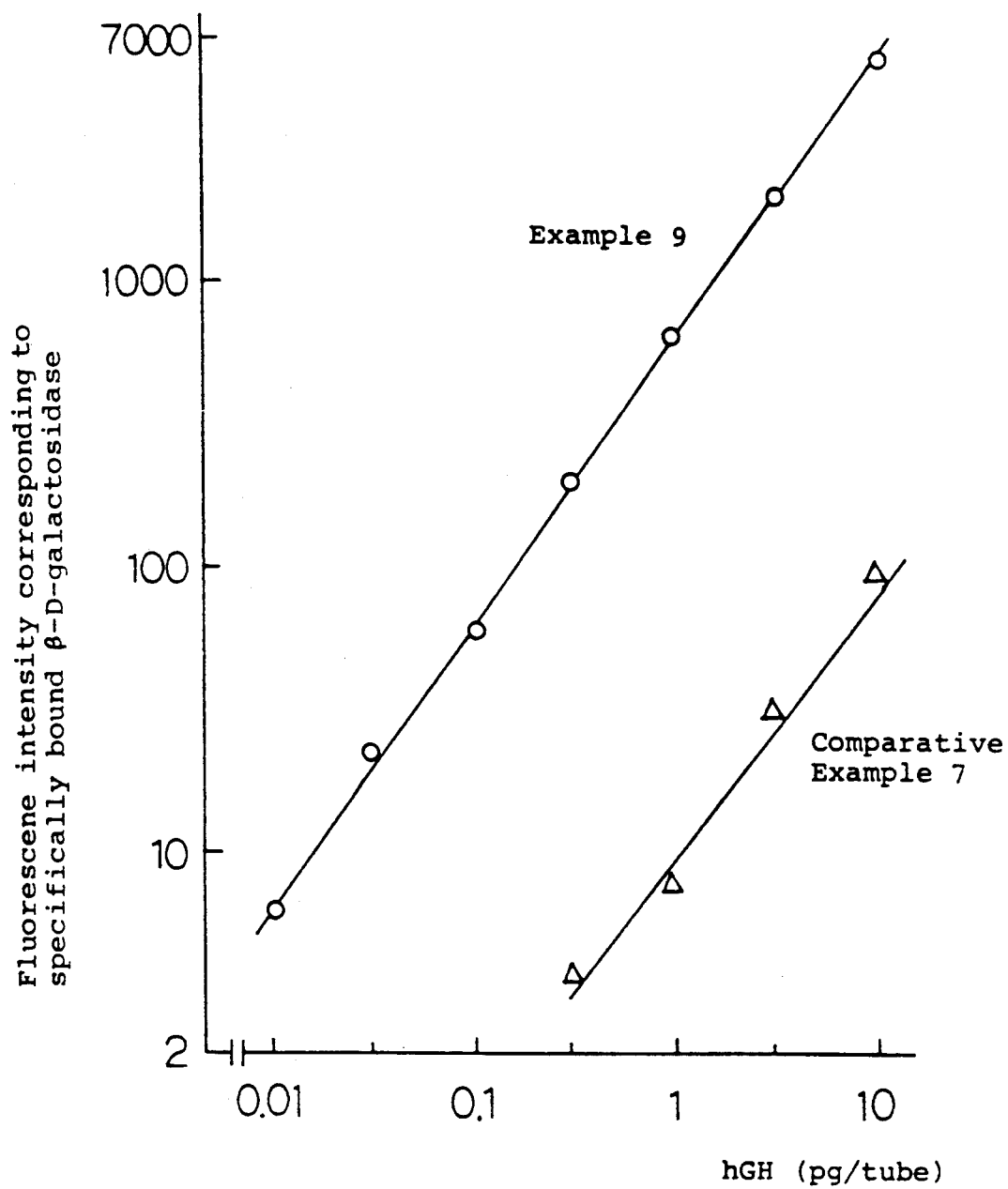
FIG_8

METHOD OF HIGH SENSITIVITY IMMUNOASSAY

This application is a continuation of application Ser. No. 227,820, filed Aug. 3, 1988, now abandoned.

BACKGROUND OF THE INVENTION

The present invention relates to a method of high sensitivity immunoassay, specifically to a method of ultrahigh sensitivity immunoassay for antigen-specific antibodies or antigenic substances.

Assay for antibodies is widely applied to examinations for infectious diseases, autoimmune diseases, etc., and it is important in examinations for autoimmune diseases, etc., to assay the component which has already formed an antigen-antibody complex in a test solution.

In addition, assay for biocomponents, in particular, antigenic substances in the body fluid of humans, is very important in clinical situations. Antigen assay is widely applied to various examinations, such as endocrine examinations by measurement of hormones, cancer diagnostic examinations and infection diagnostic examinations.

Such microdetermination for antibodies or antigenic substances has conventionally been based on immunoassay. In recent years, methods using a solid carrier have become widely used in immunoassay. Examples of such methods include methods based on sandwich technique, such as ELISA and IRMA, and methods based on competitive protein binding analysis, such as the second antibody solid phase method.

The conventional methods of immunoassay are divided into two groups: one comprises methods in which each specific antibody or antigen in the sample is trapped on an antigen- or antibody bound to a solid carrier and assayed using a labeled anti-immunoglobulin antibody or labeled antibody (art 1); the other group comprises methods in which each specific antibody is trapped on an anti-immunoglobulin antibody-coated carrier and assayed using a labeled antigen (art 2).

As an example of application of art 1, there is a report on a study of assay for human anti-insulin antibody by L. J. Nell et al., [Diabetes, 34, 60, (1985)], in which test solution was added to an insulin-bound solid carrier and bound human anti-insulin antibody was determined using enzyme labeled anti-human immunoglobulin antibody. As an example of art 2, there is a report on a study of assay for anti-toxoplasma IgM antibody by A. M. Johnson et al., [Pathology, 17, 586 (1985)], in which an anti-IgM antibody-coated solid phase was used.

In art 1, a large amount of nonspecific immunoglobulin is normally contained in the test solution, and it is absorbed nonspecifically to the solid phase to cause binding of the labeled immunoglobulin antibody; therefore, art 1 has disadvantage in that assay sensitivity decreases as a result of an increase in background value.

Also in the case of assay for antigenic substances, assay sensitivity is restricted by the background value attributable to a labeled component which is nonspecifically adsorbed onto solid carrier, and this poses a limitation on high sensitivity assay.

In art 2, there is a limitation on the capability of trapping immunoglobulin of anti-immunoglobulin antibody-coated solid carrier. Increase in carrier capability results in increase in background value. In any case, it is difficulty to obtain high sensitivity.

SUMMARY OF THE INVENTION

The object of the present invention is to provide a novel method of high sensitivity immunoassay.

The present invention comprises a method of high sensitivity immunoassay characterized by inclusion of processes (A), (B), (C) and (D) described below.

Process (A): A process of binding a solid carrier and a complex comprising the specific antibody or antigenic substance to be assayed in a test solution, and one or more active components.

Process (B): A process of dissociating said complex from the solid carrier.

Process (C): A process of binding the complex to another solid carrier.

Process (D): A process of assay for the complex on the other solid carrier, mentioned in the description of process (C) above.

BRIEF DESCRIPTION OF THE DRAWINGS

FIGS. 4 to 6 are graphs showing results of assay for anti-thyroglobulin antibody by the method of the present invention and by a conventional method.

FIGS. 7 and 8 are graphs showing results of assay for human TSH and human GH, respectively.

DETAILED DESCRIPTION OF THE INVENTION

Description of process (A)

Figure 1:
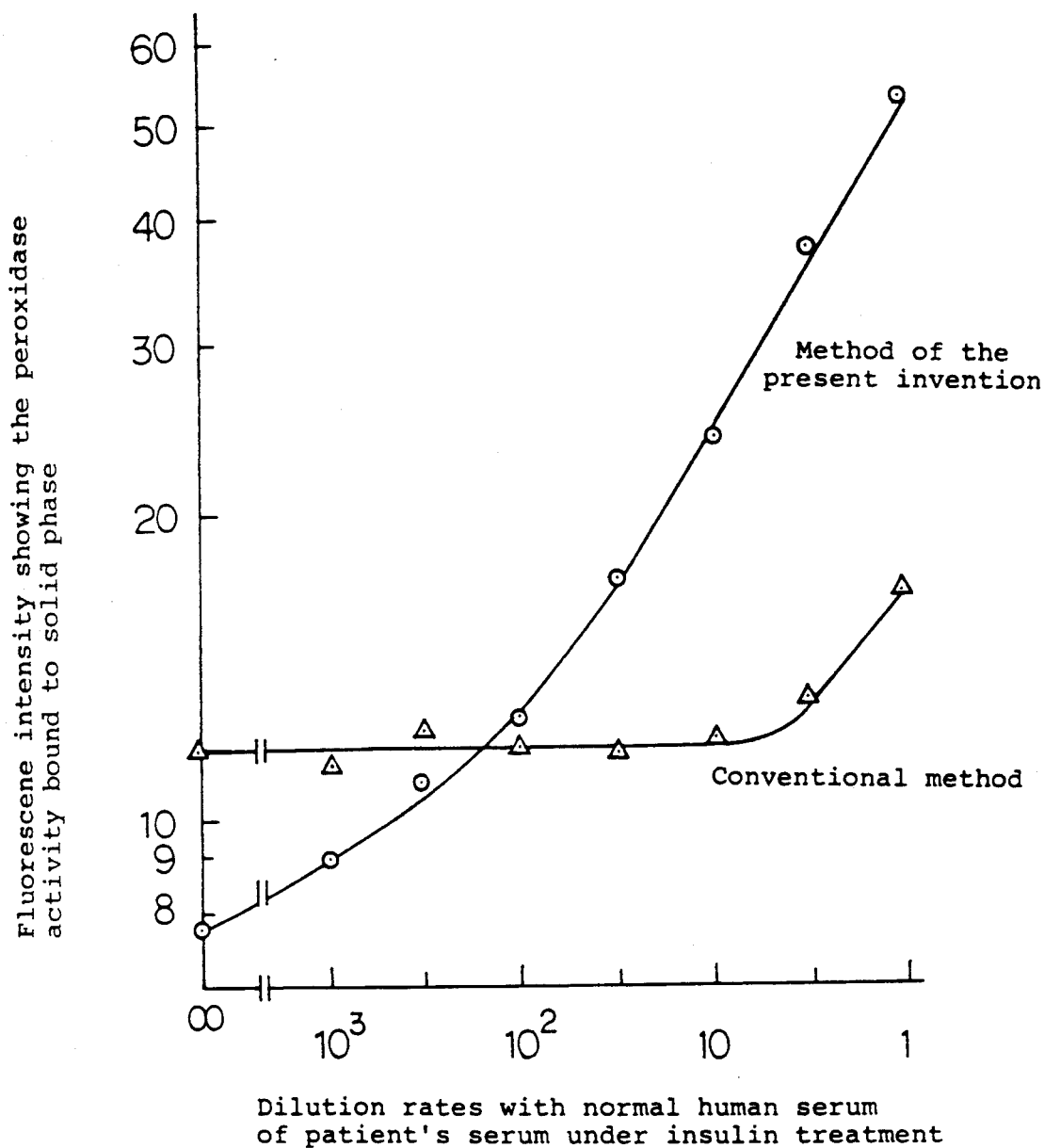
FIGS. 1 to 3 are graphs showing the results of an assay for insulin antibody by the method of the present invention and by a conventional method.

Examples of test solutions of assay include body fluids, such as serum, plasma, cerebrospinal fluid, saliva and urea, and antibody or antigen-containing buffers. Specific antibodies to be assayed include substantially all antibodies that have been successfully assayed by conventional methods of immunoassay. Examples of such antibodies include auto-antibodies, such as antinuclear antibody, anti-DNA antibody, anti-ENA antibody, rheumatoid factor, anti-erythrocyte antibody, anti-mitochondria antibody, anti-muscular antibody, anti-thyroid antibodies (anti-microsome antibody, anti-thyroglobulin antibody, anti-TSH receptor antibody), anti-insulin antibody, anti-insulin receptor antibody and anti-acetylcholine receptor antibody; antibodies against viruses or micro-organisms; antibodies against protein preparations, such as interferon and human growth hormone; and allergen antibodies in allergic diseases. These antibodies can be assayed even when they are in the form of an immune complex or a complex with bound protein, as well as in a free form in the test solution.

When the subject of assay is a specific antibody, the active components are components 1 or components 1 and 2 described below.

1. Antigen. The term antigen here means a component, such as a specific antigen or idiotypic antibody, causing antigen-antibody reaction with the antibody to be assayed.

2. A component causing antigen-antibody reaction with the above-mentioned antigen (e.g. antigens having an epitope different from that of the antibody to be assayed).

Antigenic substances to be assayed include all substances that have an antigen site, i.e. substantially all substances that have been successfully assayed by a conventional method of immunoassay. Examples of such substances include enzymes, such as γ-glutamyl transpeptidase (γ-GTP), alkaline phosphatase and glycosyltransferase; proteinous hormones, such as thyroid-stimulating hormone (TSH), luteinizing hormone (LH), human chorionic gonadotropin (hCG), insulin, secretin, and growth hormone (GH); plasma proteins, such as fibrin degradation product (FDP), C-reactive protein (CRP), $\alpha_1$-acidic glycoprotein ($\alpha_1$-AGP), $\alpha_1$-antitrypsin ($\alpha_1$-AT), $\alpha_2$-plasmin inhibitor ($\alpha_2$-PI), $\beta_2$-microglobulin ($\beta_2$-MG) and immunoglobulins; carcinoembryonic proteins, such as α-fetoprotein (AFP), carcinoembryonic antigen (CEA) and ferritin; cells, such as lymphocytes, viruses and micro-organisms; cell surface antigens; and haptens, such as digoxin, thyroxine, triiodotyrosine, cortisol and prostaglandin. These antigens can be assayed even when they are in the form of an immune complex or a complex with bound protein as well as in a free form in the test solution.

When the subject of assay is an antigenic substance, the active component is component 1 or components 1 and 2 described below.

1. Antibody. The antibody here means either of a monoclonal antibody or polyclonal antibody obtained by immunizing animals with the antigen to be assayed or a substance having the identical antigen recognition site with that of said antigen by a known method.
2. A component causing antigen-antibody reaction with the above-mentioned antibody (e.g. antigens, anti-antibodies).

These active components may normally be used in conjugation with one or more functional groups participant in the complex-carrier binding in process (A) and/or process (C).

Examples of the functional groups include haptens, such as dinitrophenyl group and trinitrophenyl group; biotin; and antibodies and antigens other than the antigen to be assayed or corresponding antibody. Said haptens and said biotin, all or which may be bound via —S—S— linkage.

The preferred functional groups are those whose binding with the solid carrier is not inhibited by any component of the test solution in process (A), which are unlikely to be eliminated by washing and which facilitate the dissociation of the complex from the solid carrier in process (B). The preferred functional groups participant in the binding in process (C) are those which are capable of efficiently binding the complex dissociated in process (B) to another solid carrier.

Furthermore, at least one of these active components may be used and labeled with a marker used for assay in process (D); in particular, a marker is bound thereto in case an antigenic substance is assayed.

Any substance can be used as marker, as long as it can be utilized for measurement in immunoassay; examples of such substances include enzymes, radioactive substances, luminescent substances, fluorescent substances and metal compounds.

Examples of useful enzymes include peroxidase, β-D-galactosidase and alkaline phosphatase; examples of useful radioactive substances include iodine and hydrogen; examples of useful fluorescent substances include fluorescein isothiocyanate; and examples of useful luminescent substances include acridium salts.

Binding of these functional groups and markers to the active component may be mediated by a soluble carrier which does not affect any of processes (A) through (D). Such mediation is particularly preferred when the active component is of low molecular weight. Examples of the soluble carrier include nonspecific rabbit IgG, bovine serum albumin and dextran.

For marker binding, there can be used any method of binding a marker to antibody or antigen in the conventional methods of immunoassay.

A solid carrier bound with a complex comprising the specific antibody or antigenic substance to be assayed in the test solution and active components can normally be prepared as follows:

Method (a): the method in which a complex comprising the specific antibody or antigenic substance to be assayed in the test solution and active components is formed, whereafter the complex is bound to a solid carrier.

Method (b): The method in which said complex is formed on a solid carrier.

Formation of a complex comprising antibody or antigen and active components is achieved by addition of one of more active components to the test solution. It is preferable that two or more active components to used, and that the active component(s) to be bound with one or more functional groups and the active component(s) to be labeled with a marker be used separately.

Conditions used for ordinary antigen-antibody reaction are used for complex formation. The complex is formed to some usually at 0° to 45° C. over a period of from several dozens of hours, preferably at 20° to 37° C. over a period of from 1 to 6 hours. The complex thus formed is bound to a solid carrier.

As the solid carrier, there can be used any substance which has been used in a conventional method of immunoassay. Examples of such substances include polystyrene, polyacrylate, Teflon, paper, glass and agarose. Furthermore, the solid carrier may have any shape.

The solid carrier needs to have a reactive group for binding the complex formed in process (A) to the solid carrier or for forming the complex on the solid carrier.

As the reactive group to be bound to the solid carrier, any reactive group which can be bound to the complex can be used, as long as it is capable of binding to the antibody or antigen to be assayed, active component, functional group, marker or immunoactive site resulting from the complex formation. The preferred reactive groups are those capable of easy dissociation of the complex in process (B).

Examples of such reactive groups include ordinary reactive groups corresponding to the functional group. For example, 1) when the functional group is a hapten, such as dinitrophenyl group or trinitrophenyl group, examples include antibodies corresponding thereto,
2) when the functional group is biotin, examples include avidin and streptoavidin, and
3) when the functional group is an antigen or antibody mediated by —S—S— linkage, examples include the corresponding antibody or antigen.

Binding of the reactive group to the solid carrier is achieved by a known method of solid carrier preparation for immunoassay.

Conditions which are normally used for the above-mentioned immunoassay using a solid carrier are used for binding the complex to the solid carrier.

The method in which active components and a solid carrier are added simultaneously into the test solution to form a complex on the carrier, namely method (b), is desirable because it permits process simplification. Description of process (B)

The solid carrier bound with the complex obtained in process (A) is subjected to process (B), usually after washing.

Conditions which are normally used for immunoassay using a solid carrier are used for washing the solid carrier bound with the complex.

It is preferable that the complex be dissociated without decomposing it. When complex-carrier binding is based on antigen-antibody reaction, it is possible to dissociate the complex by means of acid, alkali, high concentration inorganic salt, etc., by setting the binding constant for said antigen-antibody reaction below binding constant for the complex formation.

The preferred method of dissociating the complex from the solid carrier without decomposing the complex is to add a substance having the identical reactive site with that of the functional group participant in the complex-carrier binding.

For example, when the functional group is dinitrophenyl, dinitrophenyl amino acid (e.g. dinitrophenyllysine) is used; when the functional group is biotin, biotin is used; and when the functional group is an antigen, antibody, hapten, or biotin bound via —S—S— linkage, a reagent capable of breaking the —S—S— linkage is used.

DESCRIPTION OF PROCESS (C)

As the solid carrier, substances mentioned in the description of process (A) are used.

As the reactive group bound to the solid carrier, there can be used any reactive group which can be bound to the complex, as long as it is capable of binding to the antibody or antigen to be assayed, active component, functional group, marker or immunoactive site resulting from the complex formation.

Preferred reactive groups include reactive groups which are capable of binding to antigen or antibody to be assayed, active component, marker, or immunoactive site resulting from the complex formation, as well as the reactive groups mentioned in the description of process (A).

Reactive groups which can be bound to antigen or antibody to be assayed or active component by antigen-antibody reaction are particularly preferred because they permit omission of a procedure of functional group introduction.

Concerning the choice of the reactive group, it is necessary to separate the complex from the solution in which the complex has been dissociated from the solid carrier in process (B), when the used reactive group is the same as that used in process (A). For omitting this procedure of separation, it is preferable that a reactive group different from that used in process (A) be used. In such a case, it is possible to conduct the dissociation process (B) and the binding-to-the-carrier process (C) simultaneously.

For binding the complex to the solid carrier, conditions are used which are normally used for the above-mentioned immunoassay using a solid carrier, as in the case of process (A).

As regards above-mentioned processes (B) and (C), they may be repeated as necessary.

The solid carrier bound with the complex is subjected to the next process (D), usually after washing.

For washing the solid carrier conditions are used which are normally used for immunoassay using a solid carrier.

DESCRIPTION OF PROCESS (D)

For measuring the complex on the solid carrier, a known method is employed. For example, the antibody or antigenic substance to be assayed, active component, functional group, marker, and immunoactive site resulting from the complex formation, in the complex, can be used.

Examples of useful methods include a method in which an antibody that is labelled with enzyme, radioactive substance, fluorescent substance, etc., against the antibody or antigen substance to be assayed, active component or functional group, in the complex, is added, then the marker is measured after washing, and the method in which the marker introduced into the active component mentioned in the description of process (A) is measured.

The latter method is preferable because its procedure is simple. In particular, the latter method is employed when the subject of assay is an antigen.

As described above, the present invention permits a more sensitive assay for antibodies or antigenic substances assayable by a conventional method of immunoassay, as compared with the conventional methods.

Representative modes of assay for antibody are as follows:

1. An antigen as active component, previously bound with two kinds of functional groups, is bound to a solid carrier by one of the two functional groups in process (A), the complex obtained is bound to another solid carrier by the other functional group in process (C), whereby the degree of nonspecific binding of nonspecific immunoglobulin to the solid carrier is lowered in comparison with the conventional methods, and the antibody in the complex on the solid carrier is assayed by means of a labeled anti-antibody in process (D). When the anti-antibody is capable of immunoglobulin class recognition, assay is possible with discrimination of antibody immunoglobulin class.

2. An antigen as active component, previously bound with a functional group and a marker, is bound to a solid carrier by the functional group in process (A), an anti-antibody-bound solid carrier is used in process (C), whereby the degree of nonspecific binding of the labeled antigen to the solid carrier is reduced, and the marker in the complex on the solid carrier is assayed in process (D). When the anti-antibody is capable of immunoglobulin class recognition, assay is possible with discrimination of antibody immunoglobulin class.

3. When some of the antibodies are in the form of an antigen-antibody complex in the test solution, both an antigen and an antibody are used as active components. An antigen is added to make free antibody form an antigen-antibody complex, then a functional group-bound and labeled antibody is added to form an antibody-antigen-antibody complex, the resulting antibody-antigen-antibody complex is bound to a solid carrier by the functional group in process (A), a solid carrier bound with an anti-antibody against the antibody to be assayed is used in process (C), whereby the degree of nonspecific binding of the labeled antibody to the solid carrier is reduced, and the marker in the complex on the solid carrier is assayed in process (D). When the anti-antibody is capable of immunoglobulin class recognition, assay is possible with discrimination of antibody immunoglobulin class.

In addition, when it is desired to assay the antigen-antibody complex in the test solution alone, the purpose is accomplished by following the above procedure without addition of any antigen.

4. An antigen as active component, previously bound with a functional group is bound to a solid carrier by the functional group in process (A), an anti-antibody-bound solid carrier is used in process (C), whereby the degree of nonspecific binding of the labeled antigen to the solid carrier is reduced, and the antibody in the complex on the solid carrier is assayed by means of a labeled anti-antibody in process (D). When the anti-antibody is capable of immunoglobulin class recognition, assay is possible with discrimination of antibody immunoglobulin class.

Representative modes of assay for antigen are as follows:

1. For assay based on sandwich technique, different antibodies derived from two animal species are used as active components. One of the two antibodies is previously bound with a functional group, and the other is previously bound with a marker. These antibodies are bound together to form a complex, the complex thus obtained is bound to a solid carrier by the functional group in process (A), a solid carrier bound with an anti-antibody against the functional group-bound antibody is used in process (C), whereby the degree of nonspecific binding of the labeled antibody to the solid carrier is reduced, and the marker in the complex on the solid carrier is assayed in process (D).

2. When two kinds of antibodies derived from the same animal species are used as active components, one of the antibodies is previously bound with two kinds of functional groups, and the other is previously bound with a marker. These antibodies are bound together to form a complex, the complex is bound to a solid carrier by one of the functional groups in process (A), a solid carrier capable of binding to the other functional group is used in process (C), whereby the degree of nonspecific binding of the labeled antibody to the solid carrier is reduced, and the marker in the complex on the solid carrier is assayed in process (D).

3. For assay based on competitive protein binding analysis, both an antigen and an antibody are used as active components. An antigen, previously bound with a marker, and an antibody, previously bound with a functional group, are bound together to form a complex, whereafter the complex is bound to a solid carrier by the functional group in process (A), a solid carrier bound with an anti-antibody against the antibody is used in process (C), whereby the degree of nonspecific binding of the labeled antigen to the solid carrier is reduced, and the marker in the complex on the solid carrier is assayed in process (D).

As described above, the method of the present invention permits assay for all antibodies against any hapten or antigen with ultrahigh sensitivity and with discrimination of immunoglobulin class; therefore, the present method is conducive to the diagnosis of various diseases by assay for antibodies in infectious diseases, such as hepatitis B, ATL, and AIDS, auto-antibodies in autoimmune diseases, antibodies causing allergic diseases, and other antibodies.

Furthermore, the method of the present invention permits assay for antigens with ultrahigh sensitivity; therefore, the present method is also conducive to the diagnosis of various hormone secretion disorders, such as thyroid diseases and hypopituitarism, various infectious diseases, and so on.

The present invention will now be described in detail by means of the following examples, but the present invention is never limited to these examples.

EXAMPLE 1

A. Preparation of dinitrophenyl-biotinyl-nonspecific rabbit IgG-insulin conjugate (1) Preparation of maleimide-nonspecific rabbit IgG Maleimide groups were introduced into nonspecific rabbit IgG using N-succinimidyl-6-maleimidohexanoate in accordance with a known method [Hashida et al., Journal of Applied Biochemistry, 6, 56 (1984)]. The average number of maleimide groups introduced per nonspecific rabbit IgG molecule was 16.

(2) Preparation of N-biotinyl-2-mercaptoethylamine

An aliquot (0.1 ml) of 44 mM biotin-N-hydroxysuccinimide (Zymed Laboratories, Inc., San Francisco, Calif.) in N,N-dimethylformamide was incubated with 1.0 ml of 4.4 mM 2-mercaptoethylamine in 0.1M sodium phosphate buffer, pH 7.0, containing 5 mM EDTA, at 30° C. for 30 minutes, and 0.1 ml of 1M Tris-HCl buffer, pH 7.0, was added.

(3) Preparation of biotinyl-nonspecific rabbit IgG

An aliquot (0.22 ml) of N-biotinyl-2-mercaptoethylamine solution as prepared in (2) was incubated with 10 mg of maleimide-nonspecific rabbit IgG as prepared in (1) in 2.0 ml of 0.1M sodium phosphate buffer, pH 6.0, containing 5 mM EDTA at 30° C. for 30 minutes. After incubation, 0.05 ml of 0.1M 2-mercaptoethylamine solution was added to the reaction mixture, and the mixture was subjected to gel filtration on a column of Sephadex G-25 (Pharmacia).

The average number of biotin residues introduced per IgG molecule was 9.7, as calculated from the decrease in the number of maleimide groups.

(4) Preparation of mercaptosuccinyl-biotinyl-nonspecific rabbit IgG

Thiol groups were introduced into biotinyl-nonspecific rabbit IgG as prepared in (3), using S-acetyl-mercaptosuccinic anhydride (Nakarai Chemicals, Kyoto, Japan), in accordance with a known method [Ishikawa et al., Journal of Immunoassay, 4, 209 (1983)]. The average number of thiol groups introduced per biotinyl-nonspecific rabbit IgG molecule was 17.

(5) Preparation of maleimide-dinitrophenyl-L-lysine

An aliquot (1.0 ml) of 5.5 mM dinitrophenyl-L-lysine hydrochloride (Tokyo Kasei, Tokyo, Japan) in 0.1M sodium phosphate buffer, pH 7.0 was incubated with 0.1 ml of a solution of 5.5 mM N-succinimidyl-6-maleimidohexanoate in N,N-dimethylformamide at 30° C. for 30 minutes.

(6) Preparation of dinitrophenyl-biotinyl-nonspecific rabbit IgG

An aliquot (0.59 ml) of maleimide-dinitrophenyl-L-lysine as prepared in (5) was incubated with 4.4 mg of mercaptosuccinylated-biotinyl-nonspecific rabbit IgG as prepared in (4) in 3.1 ml of 0.1M sodium phosphate buffer, pH 6.0, containing 5 mM EDTA at 30° C. for 30 minutes, and the reaction mixture was subjected to gel filtration using Sephadex G-25. The average number of dinitrophenyl groups introduced per nonspecific rabbit IgG molecule was 7.3.

(7) Preparation of maleimide-insulin

Maleimide-insulin was prepared in the same manner as in (1).

(8) Preparation of dinitrophenyl-biotinyl-nonspecific rabbit IgG-insulin conjugate Maleimide-insulin (1.2 mg) as prepared in (7) in 0.3 ml of 0.1M sodium phosphate buffer, pH 6.0, containing 5 mM EDTA was incubated with mercaptosuccinylated-dinitrophenyl-biotinyl-nonspecific rabbit IgG (0.73 mg) as prepared in (6) in 0.2 ml of 0.1M sodium phosphate buffer, pH 6.0, containing 5 mM EDTA at 4° C. for 20 hours, and the reaction mixture was subjected to gel filtration on a column of Ultragel AcA 34 (LKB, Sweden).

B. Assay of anti-insulin antibody by the method of the present invention

A rabbit (anti-dinitrophenyl-bovine serum albumin) IgG-coated polystyrene ball (3.2 mm in diameter, Precision Plastic Ball Co., Chicago, Ill.) was prepared in accordance with a conventional method [Ishikawa et al., Scandinavian Journal of Immunology, 8 (supple. 7), 43 (1978)], and treated with 0.01M sodium phosphate buffer, pH 7.0, containing 2 mg/ml nonspecific rabbit IgG, 1 g/l bovine serum albumin, 0.1M NaCl, and 1 g/l NaN$_3$ (buffer A), at 20° C. for 3 hours. This polystyrene ball was incubated with 0.01 ml of human serum (sample) 0.09 ml of the above-mentioned buffer A containing 30 fmol of dinitrophenyl-biotinyl-nonspecific rabbit IgG-insulin conjugate and 0.3 mg of nonspecific rabbit IgG, and 0.05 ml of 0.01M sodium phosphate buffer, pH 7.0, containing 1M NaCl and 1 g/l bovine serum albumin at 20° C. for 4 hours. The polystyrene ball was then washed twice with 0.01M sodium phosphate buffer, pH 7.0, containing 0.1M NaCl (buffer B), and incubated with 0.15 ml of buffer A containing 1 mM dinitrophenyl-L-lysine and 0.3 mg of nonspecific rabbit IgG at room temperature overnight. After removal of the polystyrene ball, the eluate was incubated with an avidin-coated polystyrene ball treated in the same manner as above, at 20° C. for 3 hours. The polystyrene ball was then washed twice with buffer B. Anti-insulin IgG bound to this solid phase was assayed using horseradish peroxidase-labeled rabbit anti-human IgG Fab'. That is, the polystyrene ball was incubated with 50 ng of labeled Fab' in 0.15 ml of 0.01M sodium phosphate buffer, pH 7.0, containing 0.1M NaCl and 1 g/l bovine serum albumin at 20° C. for 30 minutes, after which it was washed twice with buffer B, whereafter solid phase-bound peroxidase activity was assayed by the conventional method [Imagawa et al., Analytical Letters, 16, 1509 (1983)]. The results are shown in FIG. 1.

C. Assay of anti-insulin antibody by the conventional method

A method already reported [Kohno et al., Journal of Biochemistry, 98, 379 (1985)] was used for the assay. That is, an insulin-bovine serum albumin-coated polystyrene ball (3.2 mm in diameter; Precision Plastic Ball Co., Chicago, Ill.) was incubated with serum sample at 37° C. for 3 hours and washed, after which it was incubated with horseradish peroxidase-labeled (anti-human IgG) Fab' for the assay. The results are shown in FIG. 1., i.e., FIG. 1 is a graph showing the results of assay by the method of the present invention and by the conventional method, of serum samples collected from patients who had received insulin treatment, in dilution with normal human serum, as expressed by the relationship between dilution rate for the insulin-treated patients' serum with normal human serum (abscissa) and fluorescene intensity for solid phase-bound peroxidase activity (ordinate).

As shown in FIG. 1, the method of the present invention permits anti-insulin antibody assay with an about 1000-fold higher sensitivity, as compared with the conventional method based on the above-mentioned art 1.

EXAMPLE 2

Preparation of IgG, F(ab')$_2$ and Fab'

IgG, F(ab')$_2$ and Fab' were prepared by fractionation with sodium sulfate followed by passage through a column of DEAE cellulose, by digestion of IgG with pepsin and by reduction of F(ab')$_2$, respectively, by a known method [Ishikawa et al., Journal of Immunoassay (mentioned above)].

Assay of peroxidase activity

Peroxidase activity was assayed fluorometrically by a known method using 3-(4-hydroxyphenyl)propionic acid as substrate [Imagawa et al., Analytical Letters (mentioned above.)]. The fluorescence intensity was measured relative to 1 mg/l quinine in 50 mM sulfuric acid.

Preparation of dinitrophenyl-biotinyl-nonspecific rabbit IgG-insulin conjugate

1. Preparation of maleimide-nonspecific rabbit IgG

Nonspecific rabbit IgG (12 mg) in 2.0 ml of 0.1M sodium phosphate buffer, pH 7.0 was incubated with 0.2 ml of 27.5 mM N-succinimidyl-6-maleimidohexanoate (described above) in N,N-dimethylformamide at 30° C. for 30 minutes. After incubation, the reaction mixture was subjected to gel filtration on a column (1.0×30 cm) of Sephadex G-25 (Pharmacia) using 0.1M sodium phosphate buffer, pH 6.0, containing 5 mM EDTA. The average number of maleimide groups introduced per nonspecific rabbit IgG molecule was 16.

2. Preparation of N-biotinyl-2-mercaptoethylamine

An aliquot (0.1 ml) of 44 mM biotin-N-hydroxysuccimide (Zymed Laboratories Inc., San Francisco, Calif.) in N,N-dimethylformamide was incubated with 1.0 ml of 4.4 mM 2-mercaptoethylamine in 0.1M sodium phosphate buffer, pH 7.0, containing 5 mM EDTA at 30° C. for 30 minutes. After incubation, 0.1 ml of 1M Tris-HCl buffer, pH 7.0, was added.

3. Preparation of biotinyl-nonspecific rabbit IgG

An aliquot (0.22 ml) of the N-biotinyl-2-mercaptoethylamine solution prepared in 2 was incubated with maleimide-nonspecific rabbit IgG prepared in 1 in 2.0 ml of 0.1M sodium phosphate buffer, pH 6.0, containing 5 mM EDTA, at 30° C. for 30 minutes. After incubation, 0.05 ml of 0.1M 2-mercaptoethylamine in 0.1M sodium phosphate buffer, pH 6.0, containing 5 mM EDTA was added to the reaction mixture, and the mixture was subjected to gel filtration on a column (1.0×30 cm) of Sephadex G-25 (Pharmacia) using 0.1M sodium phosphate buffer, pH 7.5. The average number of biotin residues introduced per nonspecific rabbit IgG molecule was 9.7, as calculated from the decrease in the number of maleimide groups.

4. Preparation of mercaptosuccinylated-biotinyl-nonspecific rabbit IgG.

Thiol groups were introduced into the biotinyl-nonspecific rabbit IgG prepared in 3, using S-acetylmercaptosuccinic anhydride (Nakarai Chemicals, Kyoto, Japan) in accordance with a known method [Ishikawa et al., Journal of Immunoassay (mentioned above)]. The average number of thiol groups introduced per biotinyl-nonspecific rabbit IgG molecule was 17.

5. Preparation of maleimide-dinitrophenyl-L-lysine

An aliquot (1.0 ml) of 5.5 mM dinitrophenyl-L-lysine hydrochloride (Tokyo Kasei, Tokyo, Japan) in 0.1M sodium phosphate buffer, pH 7.0, was incubated with 0.1 ml of 5.5 mM N-succinimidyl-6-maleimidohexanoate in N,N-dimethylformamide at 30° C. for 30 minutes.

6. Preparation of mercaptosuccinylated dinitrophenyl biotinyl-nonspecific rabbit IgG.

An aliquot (0.59 ml) of the maleimide-dinitrophenyl-L-lysine solution prepared in 5 was incubated with 4.4 mg of the mercaptosuccinylated biotinyl nonspecific rabbit IgG prepared in 4 in 3.1 ml of 0.1M sodium phosphate buffer, pH 6.0, containing 5 mM EDTA at 30° C. for 30 minutes. The reaction mixture was subjected to gel filtration on a column (1.0×30 cm) of Sephadex G-25 (Pharmacia) using 0.1M sodium phosphate buffer, pH 6.0, containing 5 mM EDTA. The average number of dinitrophenyl groups introduced per mercapto-succinylated biotinyl nonspecific rabbit IgG molecule was 7.3, as calculated from the absorbance at 360 nm by taking the molar extinction coefficient to be 17,400 $mol^{-1}.l.cm^{-1}$.

7. Preparation of maleimide-insulin

Porcine insulin (40 IU in 1.0 ml, Actrapid MC, Novo) was incubated with 0.1 ml of 4.4 mM N-succinimidyl-6-maleimidohexanoate in N,N-dimethylformamide at 30° C. for 30 minutes and subjected to gel filtration on the column (1.0×30 cm) of Sephadex G-25 (Pharmacia) using 0.1M sodium phosphate buffer, pH 6.0, containing 5 mM EDTA. The average number of maleimide groups introduced per porcine insulin molecule was 0.23. The amount of insulin was calculated from the absorbance at 280 nm by taking the extinction coefficient to be 0.9 $g^{-1}.l.cm^{-1}$ and the molecular weight to be 5,778.

8. Preparation of dinitrophenyl biotinyl nonspecific rabbit IgG-insulin conjugate.

Maleimide-insulin (1.2 mg) prepared in 7 in 0.3 ml of 0.1M sodium phosphate buffer, pH 6.0, containing 5 mM EDTA was incubated with mercaptosuccinylated dinitrophenyl biotinyl-nonspecific IgG (0.73 mg) prepared in 6 (7 thiol groups per molecule) in 0.2 ml of 0.1M sodium phosphate buffer, pH 6.0, containing 5 mM EDTA at 4° C. for 20 hours. After incubation, the reaction mixture was subjected to gel filtration on a column (1.5×45 cm) of Ultrogel AcA34 (LKB, Stockholm, Sweden) using 0.1M sodium phosphate buffer, pH 6.5. The average number of insulin molecules conjugated per dinitrophenyl-biotinyl-nonspecific rabbit IgG molecule was 5.8. The amount of dinitrophenyl-biotinyl-nonspecific rabbit IgG molecules was calculated from the absorbance at 360 nm and the number of insulin molecules introduced was calculated from the absorbance at 280 nm.

Preparation of rabbit (anti-dinitrophenyl-bovine serum albumin) IgG- or avidin-coated solid phase Polystyrene balls (3.2 mm in diameter; Precision Plastic Ball Co., Chicago) were coated by physical adsorption with rabbit (anti-dinitrophenyl-bovine serum albumin) IgG solution (0.1 g/l) or avidin solution (0.1 g/l) by a known method [Ishikawa et al., Scandinavian Journal of Immunology (mentioned above)].

Pretreatment of coated solid phase

The coated solid phase was pretreated with nonspecific rabbit IgG by a known method [Kohno et al., Journal of Biochemistry (mentioned above)] before use.

Preparation of rabbit (anti-human IgG γ-chain) Fab'-peroxidase

Rabbit (anti-human IgG γ-chain) Fab' was conjugated with horseradish peroxidase by a known method [Hashida et al., Journal of Applied Biochemistry (mentioned above)] using N-succinimidyl-6-maleimidohexanoate as crosslinking agent.

Preparation of dextran-charcoal

The dextran-charcoal was prepared by the method of Dickson [Dickson, Clinical Chemistry, 20, 1275 (1974)] with the following substitutions. Human serum albumin and Norit NK were substituted by bovine serum albumin and Norit A (Nakarai Chemicals, Kyoto, Japan), respectively. The dextran-charcoal suspension contained 60 mg of dextran-charcoal in dry weight per ml.

Dextran-charcoal treatment of serum samples

A 0.075 ml aliquot of serum samples, prepared by diluting serum of diabetics who had received insulin treatment with normal human serum at various dilution rates, was adjusted to pH 6.0 by the addition of 0.015 ml of 0.2M HCl. To this mixture, 0.0375 ml of the dextran-charcoal suspension was added, and this was followed by 5 minutes of agitation. Subsequently, 0.015 ml of 50 mM NaOH was added to neutralize the mixture. The neutralized mixture was centrifuged at 1,500 g for 15 minutes. The supernatant was centrifuged using the same conditions as above.

Assay of anti-insulin antibody

Figure 2:
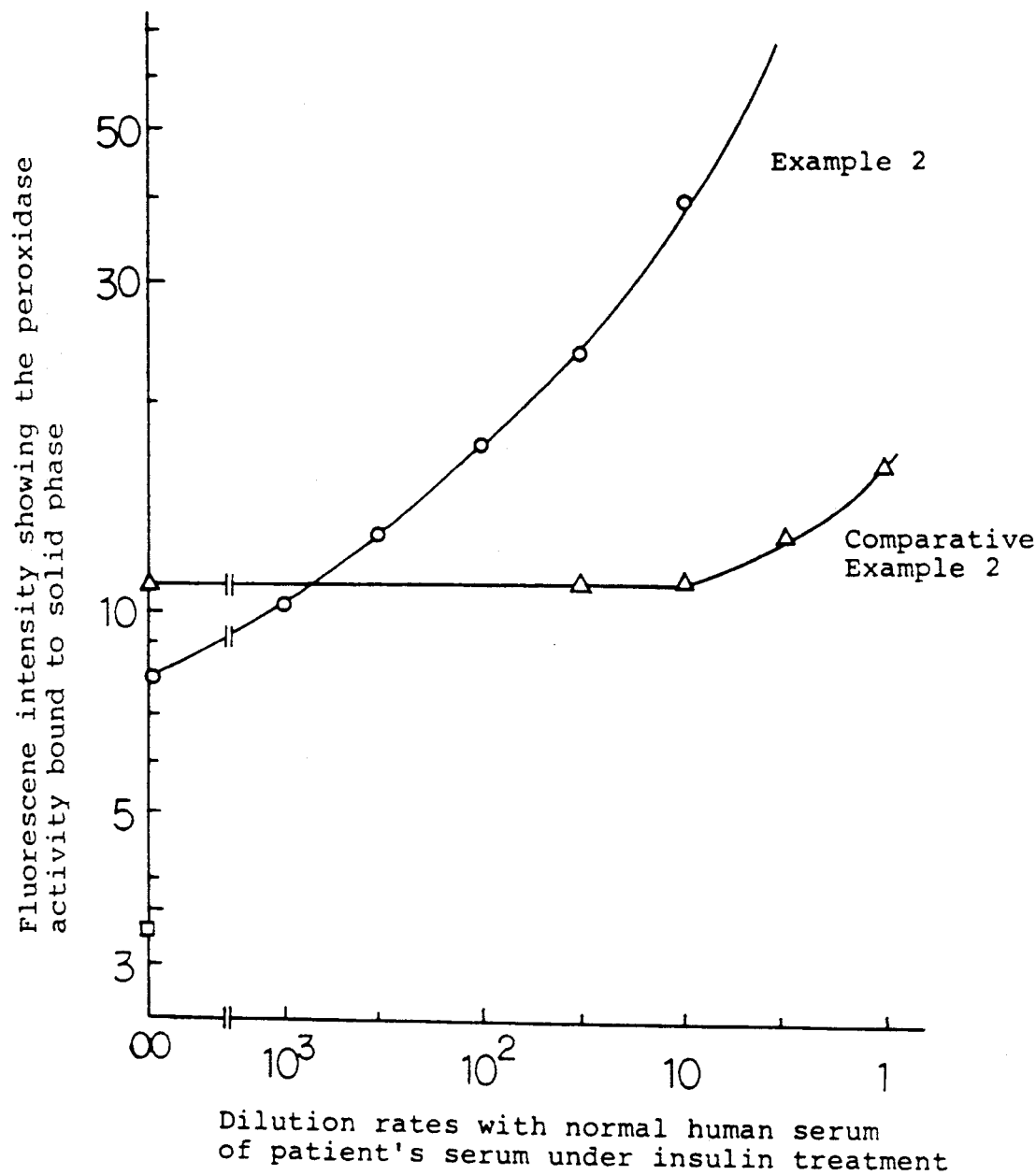

An aliquot (0.095 ml) of the dextran-charcoal-treated serum sample was mixed with 0.015 ml of 0.03M sodium phosphate buffer, pH 7.0, containing 0.3% $NaN_3$, 3.1M NaCl and 0.3% bovine serum albumin and 0.02 ml of 0.01M sodium phosphate buffer, pH 7.0, containing 1.5% nonspecific rabbit IgG, 0.1% $NaN_3$, 0.1M NaCl and 0.1% bovine serum albumin, and incubated with 30 fmol of dinitrophenyl-biotinyl-nonspecific rabbit IgG-insulin conjugate in 0.02 ml of 0.01M sodium phosphate buffer, pH 6.0, containing 0.1% $NaN_3$, 0.1M NaCl and 0.1% bovine serum albumin at 37° C. for 8 hours and at room temperature overnight. The reaction mixture was further incubated with a rabbit (anti-dinitrophenyl-bovine serum albumin) IgG-coated polystyrene ball at 20° C. for 4 hours. The polystyrene ball was washed twice with 2 ml of 0.01M sodium phosphate buffer, pH 7.0, containing 0.1M NaCl, and incubated with 150 nmol of dinitrophenyl-L-lysine in 0.15 ml of 0.01M sodium phosphate buffer, pH 7.0, containing 0.1% $NaN_3$, 0.1M NaCl, 0.2% nonspecific rabbit IgG and 0.1% bovine serum albumin, at room temperature overnight. After removal of the polystyrene ball, the eluate was incubated with an avidin-coated polystyrene ball at 20° C. for 3 hours. The polystyrene ball was then washed twice with 2 ml of 0.01M sodium phosphate buffer, pH 7.0, containing 0.1M NaCl as described above and incubated with 50 ng of rabbit (anti-human IgG γ-chain) Fab'-peroxidase conjugate in 0.15 ml of 0.01M sodium phosphate buffer, pH 7.0, containing 0.1M NaCl and 0.1% bovine serum albumin at 20° C. for 3 hours. After washing the polystyrene ball as described above, peroxidase activity bound to the polystyrene ball was assayed at 30° C. for 10 minutes. As shown in FIG. 2, assay was possible up to $10^3$-fold dilution.

COMPARATIVE EXAMPLE 2

Assay of peroxidase activity, preparation of rabbit (anti-human IgG γ-chain) Fab'-peroxidase and dextran-charcoal treatment of serum samples were conducted in accordance with the methods of Example 2.

Preparation of insulin-bovine serum albumin-coated solid phase

The coated solid phase was prepared by coating a polystyrene ball with bovine serum albumin (1.0 g/l) in the same manner as in Example 2, activating the polystyrene ball by a known method using glutaraldehyde [Kohno et al., Journal of Biochemistry (mentioned above)], and subsequently reacting with insulin.

Assay of anti-insulin antibody

The sample treated with dextran-charcoal in Example 2 was diluted $5.3 \times 10^4$-fold with 0.01M sodium phosphate buffer, pH 7.0, containing 0.1% NaN$_3$ and 0.1M NaCl and 0.1% bovine serum albumin. The diluted serum sample (0.15 ml) was incubated with the insulin-bovine serum albumin-coated polystyrene ball at 37° C. for 3 hours. The polystyrene ball was then washed twice with 2 ml of 0.01M sodium phosphate buffer, pH 7.0, containing 0.1M NaCl, and incubated with 50 ng of rabbit (anti-human IgG γ-chain) Fab'-peroxidase conjugate in 0.01M sodium phosphate buffer, pH 7.0, containing 0.1M NaCl and 0.1% bovine serum albumin at 37° C. for 3 hours. After washing the polystyrene ball in the same manner as above, peroxidase activity bound to the polystyrene ball was assayed at 30° C. for 10 minutes. As shown in FIG. 2, assay was possible up to 1-fold dilution.

The method of Example 2 according to the present invention permits assay of serum anti-insulin antibody with higher sensitivity as compared with the conventional method of Comparative Example 2.

EXAMPLE 3

Assay of peroxidase activity, preparation of IgG-coated solid phase, pretreatment of coated solid phase and preparation of dextran-charcoal were conducted in accordance with the methods of Example 2.

Preparation of dinitrophenyl-bovine serum albumin-insulin-peroxidase conjugate 1. Preparation of mercaptosuccinylated bovine serum albumin Thiol groups were introduced into bovine serum albumin (fraction V, Armour Pharmaceutical Co., Kankakee, Ill.) by a known method using S-acetylmercaptosuccinic anhydride [Ishikawa et al., Journal of Immunoassay (mentioned above)]. The average number of thiol groups introduced per bovine serum albumin molecule was 8.2.

2. Preparation of maleimide-dinitrophenyl-L-lysine

An aliquot (1.5 ml) of 5.5 mM dinitrophenyl-L-lysine hydrochloride in 0.1M sodium phosphate buffer, pH 7.0, containing 5 mM EDTA was incubated with 0.15 ml of 5.5 mM N-succinimidyl-6-maleimidohexanoate in N,N-dimethylformamide at 30° C. for 30 minutes.

3. Preparation of dinitrophenyl-bovine serum albumin

The mercaptosuccinylated bovine serum albumin (5 mg) in 1.0 ml of 0.1M sodium phosphate buffer, pH 6.0, containing 5 mM EDTA was incubated with 1.5 ml of the maleimide-dinitrophenyl-L-lysine solution at 30° C. for 30 minutes. The reaction mixture was subjected to gel filtration on a column (1.5×45 cm) of Sephadex G-25 using 0.1M sodium phosphate buffer, pH 7.5. The average number of dinitrophenyl groups introduced per bovine serum albumin molecule was 5.5.

4. Preparation of mercaptosuccinylated dinitrophenyl-bovine serum albumin

Thiol groups were introduced into dinitrophenyl-bovine serum albumin by a known method using S-acetylmercaptosuccinic anhydride [Ishikawa et al., Journal of Immunoassay (mentioned above)]. The average number of thiol groups introduced per dinitrophenyl-bovine serum albumin molecule was 7.0.

5. Preparation of maleimide-insulin and maleimide-peroxidase

Maleimide groups were introduced into porcine insulin (Actrapid MC., Novo Industri A/S, Copenhagen, Denmark) and horseradish peroxidase (grade I, Boehringer Mannheim GmbH, Mannheim, West Germany) by a known method using N-succinimidyl-6-maleimidohexanoate [Hashida et al., Journal of Applied Biochemistry (mentioned above)]. The average numbers of maleimide groups introduced per insulin molecule and peroxidase molecule were 0.9 and 1.1, respectively.

6. Preparation of dinitrophenyl-bovine serum albumin-insulin-peroxidase conjugate The mercaptosuccinylated dinitrophenyl bovine serum albumin (1.9 mg) in 0.5 ml of 0.1M sodium phosphate buffer, pH 6.0, containing 5 mM EDTA was incubated with 1.7 mg of maleimide-insulin in 0.3 ml of 0.1M sodium phosphate buffer, pH 6.0, containing 5 mM EDTA, and 1.7 mg of maleimide-peroxidase in 0.2 ml of 0.1M sodium phosphate buffer, pH 6.0, containing 5 mM EDTA at 30° C. for 2 hours. The reaction mixture was subjected to gel filtration on a column (1.5×45 cm) of Ultrogel AcA 44 using 0.1M sodium phosphate buffer, pH 6.5. The average numbers of insulin molecules and peroxidase molecules conjugated per bovine serum albumin molecule were 3.8 and 2.0, respectively.

Preparation of protein-Sepharose 4B

Dinitrophenyl-bovine serum albumin (10 mg) and human IgG (10 mg) were each coupled to CNBr-activated Sepharose 4B (1 g) according to the instructions of Pharmacia.

Affinity-purification of IgG

Rabbit (anti-dinitrophenyl-bovine serum albumin) IgG (Miles Co., Elkhart, Ind.) and rabbit (anti-human IgG γ-chain) IgG (Medical and Biological Laboratories, Nagoya, Japan) were affinity-purified by elution at pH 2.5 from columns of dinitrophenyl-bovine serum albumin-coupled Sepharose 4B and human IgG-coupled Sepharose 4B, respectively, by a known method [Kohno et al., Journal of Biochemistry (mentioned above)].

Dextran-charcoal treatment of serum samples

An aliquot (1.0 ml) of serum sample prepared by diluting serum of diabetics who had received insulin treatment with normal human serum at various dilution rates was adjusted to pH 6.0 by the addition of 0.2 ml of 0.2M HCl. After addition of 0.5 ml of the dextran-charcoal suspension followed by 5 minutes of agitation, 0.2 ml of 50 mM NaOH was added to neutralize the mixture. The neutralized mixture was centrifuged at 1,500 g for 15 minutes, and the resulting supernatant was centrifuged using the same conditions as above.

Assay of anti-insulin antibody

Figure 3:
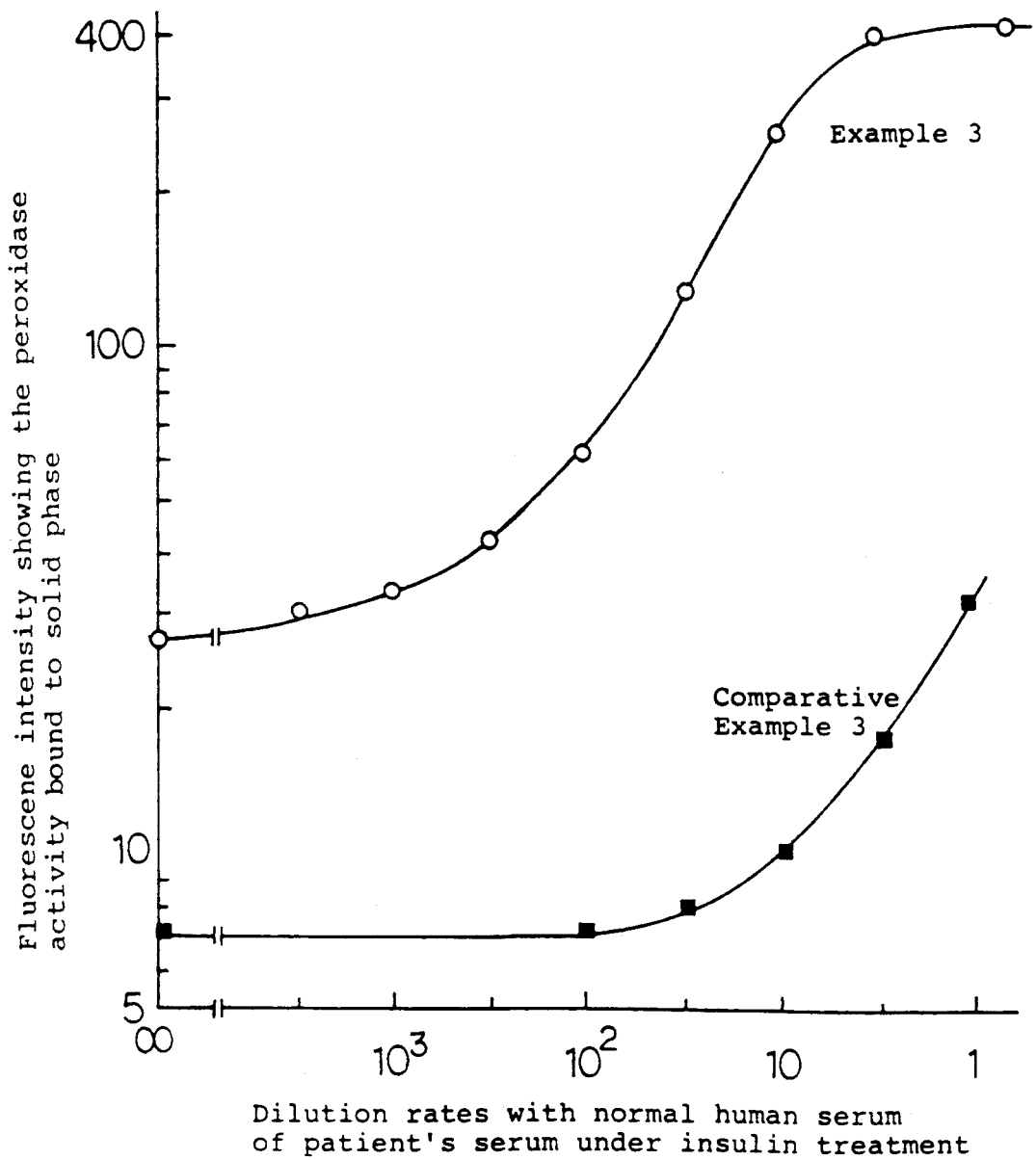

The two affinity-purified rabbit (anti-dinitrophenyl-bovine serum albumin) IgG-coated polystyrene balls were incubated with 0.019 ml of the dextran-charcoal treated serum, 0.081 ml of 0.01M sodium phosphate buffer, pH 7.0, containing 15 fmol of dinitrophenyl-bovine serum albumin-insulin-peroxidase conjugate, 0.37% nonspecific rabbit IgG, 0.1M NaCl and 0.1% bovine serum albumin and 0.05 ml of 0.01M sodium phophate buffer, pH 7.0, containing 1M NaCl and 0.1% bovine serum albumin at 20° C. for 3 hours. The polystyrene balls were then washed twice with 2 ml of 0.01M sodium phosphate buffer, pH 7.0, containing 0.1M NaCl and incubated with 150 nmol of dinitrophenyl-L-lysine in 0.15 ml of 0.01M sodium phosphate buffer, pH 7.0, containing 0.1M NaCl and 0.1% bovine serum albumin, and two affinity-purified rabbit (anti-human IgG γ-chain) IgG-coated polystyrene balls, at 20° C. for 3 hours. After washing the affinity-purified rabbit (anti-human IgG) IgG-coated polystyrene balls in the same manner as above, peroxidase activity bound to the polystyrene was assayed at 30° C. for 10 minutes. As shown in FIG. 3, assay was possible up to $10^3$-fold dilution.

COMPARATIVE EXAMPLE 3

Assay of peroxidase activity and preparation of IgG-coated solid phase were conducted in accordance with the methods of Example 2. Affinity-purification of rabbit (anti-human IgG γ-chain) IgG and dextran-charcoal treatment of serum sample were conducted in accordance with the methods of Example 3.

Preparation of insulin-peroxidase

1. Preparation of mercaptosuccinylated insulin

Thiol groups were introduced into insulin using S-acetyl-mercaptosuccinic anhydride in the same manner as in Example 2. The number of thiol groups introduced per insulin molecule was 0.46.

2. Preparation of insulin-peroxidase

The mercaptosuccinylated insulin (4 mg) in 5.7 ml of 0.1M sodium phosphate buffer, pH 6.0, containing 5 mM EDTA was incubated with 2.4 mg of the maleimide-peroxidase prepared in Example 3 in 0.6 ml of 0.1M sodium phosphate buffer, pH 6.0, containing 5 mM EDTA at 4° C. for 20 hours. The reaction mixture was subjected to gel filtration on a column (2.0×40 cm) of Ultrogel AcA 44 using 0.1M sodium phosphate buffer, pH 6.5. The average number of insulin molecules conjugated per peroxidase molecule was 1.6.

Assay of anti-insulin antibody

The sample treated with dextran-charcoal in Example 3 was diluted $2.6 \times 10^4$-fold with 0.01M sodium phosphate buffer, pH 7.0, containing 0.1% NaN$_3$, 0.1M NaCl and 0.1% bovine serum albumin. An affinity-purified rabbit (anti-human IgG γ-chain) IgG-coated polystyrene ball was incubated with 0.15 ml aliquot of this diluted serum at 37° C. for 3 hours. The polystyrene ball was washed twice with 2 ml of 0.01M sodium phosphate buffer, pH 7.0, containing 0.1M NaCl and incubated with 50 ng of insulin-peroxidase conjugate in 0.15 ml of 0.01M sodium phosphate buffer, pH 7.0, containing 0.1M NaCl and 0.1% bovine serum albumin, at 37° C. for 3 hours. After washing the polystyrene ball in the same manner as above, peroxidase activity bound to the polystyrene ball was assayed at 30° C. for 10 minutes. As shown in FIG. 3, assay was possible up to $3 \times 10$-fold dilution.

The method of Example 3 according to the present invention permits assay of serum anti-insulin antibody with higher sensitivity as compared with the conventional methods of Comparative Examples 2 and 3.

EXAMPLE 4

Assay of peroxidase activity, preparation of IgG-coated solid phase, pretreatment of coated solid phase, preparation of IgG, F(ab')$_2$ and Fab', and preparation of rabbit (anti-human IgG γ-chain) Fab'-peroxidase were conducted in accordance with the methods of Example 2. Preparation of dinitrophenyl-bovine serum albumin, preparation of protein-Sepharose 4B, and affinity-purification of IgG were conducted in accordance with the methods of Example 3.

Purification of thyroglobulin

Crude thyroglobulin, which had been prepared from thyroid glands by fractionation with ammonium sulfate [Roitt et al., Lancet, 15, 1027 (1958)], was further purified by chromatography on a column of DEAE cellulose [Ohtaki et al., Journal of Clinical Endocrinology and Metabolite, 52, 239 (1981)].

The above purified thyroglobulin (3.0 mg) in 1.5 ml of 0.1M sodium phosphate buffer, pH 7.0, containing 0.1% NaN$_3$ was passed through a column (0.9×5.5 cm) of rabbit (anti-human IgG γ-chain) IgG Sepharose 4B using the same buffer, and subjected to gel filtration on a column (1.5×45 cm) of Ultrogel AcA 22 using the same buffer. Homogeneity of the purified thyroglobulin was confirmed by SDS polyacrylamide gel electrophoresis in the presence of urea. The amount of thyroglobulin was calculated from the absorbance at 280 nm by taking the extinction coefficient to be 1.0 $g^{-1}.l.cm^{-1}$.

Preparation of dinitrophenyl-thyroglobulin

1. Preparation of mercaptosuccinylated thyroglobulin

Thiol groups were introduced into purified thyroglobulin by a known method using S-acetylmercaptosuccinic anhydride [Ishikawa et al., Journal of Immunoassay (mentioned above)]. The number of thiol groups introduced per thyroglobulin molecule was 20.

2. Preparation of maleimide-dinitrophenyl-L-lysine

Maleimide-dinitrophenyl-L-lysine was prepared in the same manner as in Example 3.

3. Preparation of dinitrophenyl-thyroglobulin

The mercaptosuccinylated thyroglobulin (0.5 mg) in 1.0 ml of 0.1M sodium phosphate buffer, pH 6.0, containing 5 mM EDTA was incubated with 0.03 ml of maleimide-dinitrophenyl-L-lysine solution at 30° C. for 30 minutes, and subsequently with 5 μl of 0.1M N-ethylmaleimide in the same buffer at 30° C. for 15 minutes. The reaction mixture was subjected to gel filtration on a column (1×30 cm) of Sephadex G-25 using 0.1M sodium phosphate buffer, pH 7.0, containing 0.1% NaN$_3$. The average number of dinitrophenyl groups introduced per thyroglobulin molecule was 16.

Assay of anti-thyroglobulin antibody

Figure 4:
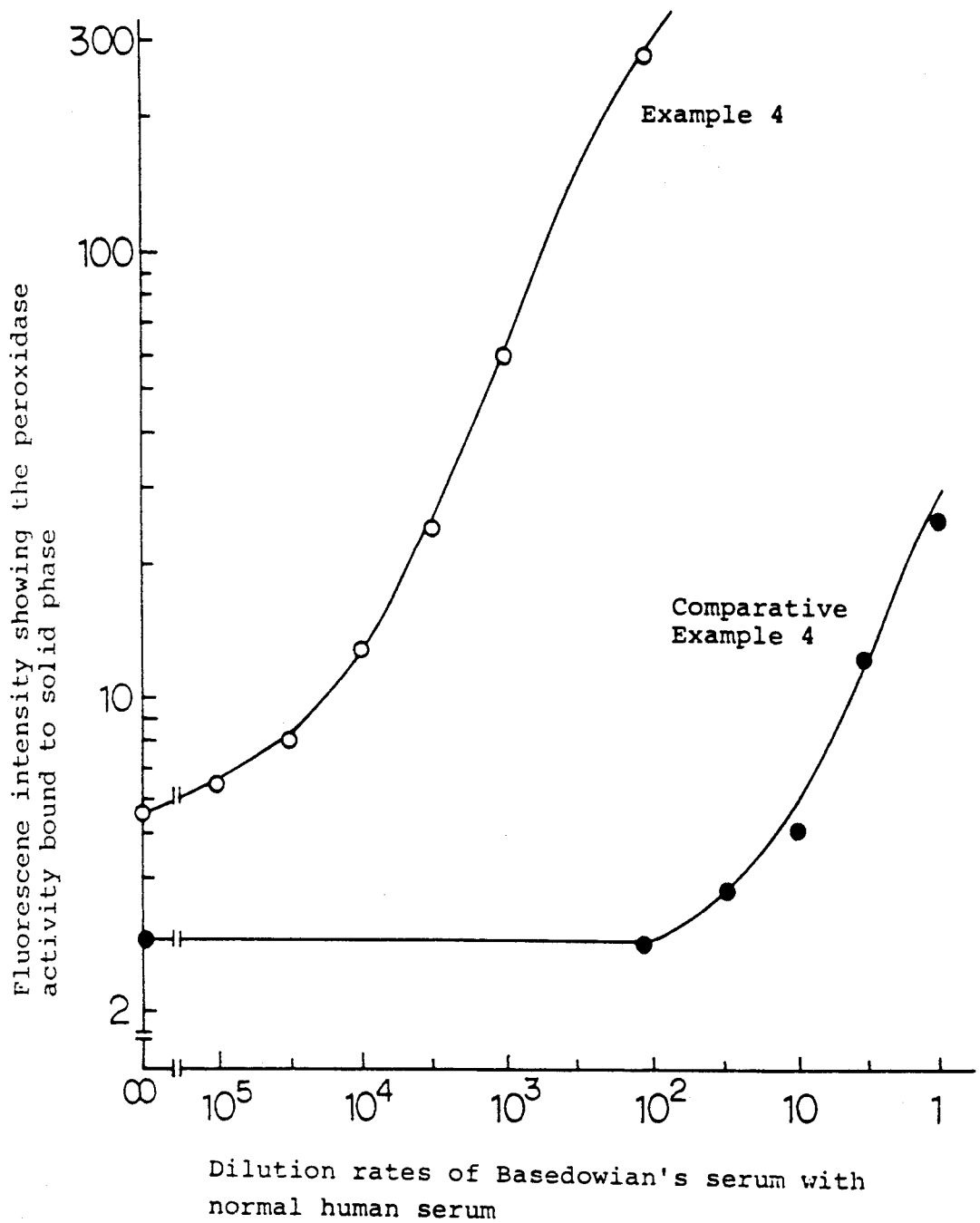

An aliquot (0.02 ml) of sample prepared by diluting human serum containing anti-thyroglobulin antibody with normal human serum at various dilution rates was incubated with 0.08 ml of 0.01M sodium phosphate buffer, pH 7.0, containing 50 fmol of dinitrophenyl-thyroglobulin, 0.375% nonspecific rabbit IgG, 0.1% $NaN_3$, 0.1M NaCl and 0.1% bovine serum albumin, 0.05 ml of 0.01M sodium phosphate buffer, pH 7.0, containing 0.1% $NaN_3$, 1M NaCl and 0.1% bovine serum albumin, and an affinity-purified rabbit (anti-dinitrophenyl-bovine serum albumin) IgG-coated polystyrene ball, at 20° C. for 20 hours. The polystyrene ball was then washed twice with 2 ml of 0.01M sodium phosphate buffer, pH 7.0, containing 0.1M NaCl, and incubated with 150 nmol of dinitrophenyl-L-lysine in 0.15 ml of 0.01M sodium phophate buffer, pH 7.0, containing 0.2% nonspecific rabbit IgG, 0.1% $NaN_3$, 0.1M NaCl and 0.1% bovine serum albumin at 20° C. for 3 hours. After removal of the polystyrene ball, the eluate was incubated with a rabbit (anti-thyroglobulin) IgG-coated polystyrene ball at 20° C. for 3 hours. The polystyrene ball was then washed in the same manner as above, and incubated with 50 ng of rabbit (anti-human IgG γ-chain) Fab'-peroxidase conjugate in 0.15 ml of 0.01M sodium phosphate buffer, pH 7.0, containing 0.1M NaCl and 0.1% bovine serum albumin, at 20° C. for 3 hours. After washing the polystyrene ball in the same manner as above, peroxidase activity bound to the polystyrene ball was assayed at 30° C. for 10 minutes. As shown in FIG. 4, assay was possible up to $10^5$-fold dilution.

COMPARATIVE EXAMPLE 4

Assay of peroxidase activity, preparation of IgG-coated solid phase, and preparation of rabbit (anti-human IgG γ-chain) Fab'-peroxidase were conducted in accordance with the methods of Example 2. Purification of thyroglobulin was conducted in accordance with the method of Example 4.

Preparation of thyroglobulin-coated solid phase

Thyroglobulin (0.1 g/l) was coated by physical adsorption to polystyrene ball in the same manner as in Example 2.

Assay of antithyroglobulin antibody

A sample prepared by diluting human serum containing anti-thyroglobulin antibody with normal human serum at various dilution rates was diluted $1 \times 10^5$-fold with 0.01M sodium phosphate buffer, pH 7.0, containing 0.1% $NaN_3$, 0.1M NaCl and 0.1% bovine serum albumin. An aliquot (0.15 ml) of this diluted serum was incubated with a thyroglobulin-coated polystyrene ball at 37° C. for 3 hours. The polystyrene ball was then washed twice with 2 ml of 0.01M sodium phosphate buffer, pH 7.0, containing 0.1M NaCl, and incubated with 50 ng of rabbit (anti-human IgG γ-chain) Fab'-peroxidase conjugate in 0.15 ml of 0.01M sodium phosphate buffer, pH 7.0, containing 0.1M NaCl and 0.1% bovine serum albumin, at 37° C. for 3 hours. After washing the polystyrene ball in the same manner as above, peroxidase activity bound to the polystyrene ball was assayed at 30° C. for 10 minutes. As shown in FIG. 4, assay was possible up to $10 \times 5$-fold dilution.

EXAMPLE 5

Assay of peroxidase activity, preparation of IgG-coated solid phase, preparation of biotinyl-nonspecific rabbit IgG, and preparation of rabbit (anti-human IgG γ-chain) Fab'-peroxidase were conducted in accordance with the methods of Example 2. Preparation of protein-Sepharose 4B and affinity-purification of IgG were conducted in accordance with the methods of Example 3. Purification of thyroglobulin was conducted in accordance with the method of Example 4.

Preparation of dinitrophenyl-biotinyl-nonspecific rabbit IgG-affinity-purified anti-thyroglobulin Fab'

1. Preparation of mercaptosuccinylated nonspecific rabbit IgG

Nonspecific rabbit IgG (4.0 mg) in 1.5 ml of 0.1M sodium phosphate buffer, pH 7.5, was incubated with 0.15 ml of 0.11M S-acetyl-mercaptosuccinic anhydride (Nakarai Chemicals, Kyoto, Japan) in N,N-dimethylformamide at 30° C. for 30 minutes. After incubation, the mixture was incubated with 0.1M Tris-HCl buffer, pH 7.0 (0.15 ml), 0.1M EDTA, pH 7.0 (0.1 ml) and 1M hydroxylamine, pH 7.0 (0.25 ml) at 30° C. for 15 minutes. The mixture was subjected to gel filtration on a column (1.0×30 cm) of Sephadex G-25 using 0.1M sodium phosphate buffer, pH 6.0, containing 5 mM EDTA. The average number of thiol groups introduced per nonspecific rabbit IgG molecule was 16.

2. Preparation of maleimide-dinitrophenyl-L-lysine

An aliquot (1.5 ml) of 8.8 mM dinitrophenyl-L-lysine (Tokyo Kasei, Tokyo, Japan) in 0.1M sodium phosphate buffer, pH 7.0, containing 5 mM EDTA was incubated with 0.15 ml of 8.8 mM N-succinimidyl-6-maleimidohexanoate (Dojin Kagaku, Kumamoto; Japan) in N,N-dimethylformamide at 30° C. for 30 minutes.

3. Preparation of dinitrophenyl-nonspecific rabbit IgG

The mercaptosuccinylated nonspecific rabbit IgG (3.0 mg) in 0.1M sodium phosphate buffer, pH 6.0 (1.8 ml), containing 5 mM EDTA was incubated with 1.5 ml of maleimide-dinitrophenyl-L-lysine at 30° C. for 30 minutes. After incubation, the reaction mixture was subjected to gel filtration on a column (1.0×30 cm) of Sephadex G-25 using 0.1M sodium phosphate buffer, pH 7.0. The average number of dinitrophenyl groups introduced per nonspecific rabbit IgG molecule was 11.9. Determination of dinitrophenyl groups was performed spectro-photometrically.

4. Preparation of maleimide-dinitrophenyl-nonspecific rabbit IgG.

The dinitrophenyl-nonspecific rabbit IgG (2.4 mg) in solution in 0.1M sodium phosphate buffer, pH 7.0 (3.0 ml), was incubated with 88 mM N-succinimidyl-6-maleimidohexanoate in N,N-dimethylformamide (0.3 ml) at 30° C. for 30 minutes, and the reaction mixture was subjected to gel filtration on a column (1.0×30 cm) of Sephadex G-25 using 0.1M sodium phosphate buffer, pH 6.0, containing 5 mM EDTA. The average number of maleimide groups introduced per dinitrophenyl-nonspecific rabbit IgG molecule was 18.

5. Preparation of N-biotinyl-2-mercaptoethylamine

An aliquot (0.2 ml) of 44 mM biotin-N-hydroxysuccimide (Zymed Laboratories, San Francisco, Calif. in N,N-dimethylformamide was incubated with 2.0 ml of 4.4 mM mercaptoethylamine in 0.1M sodium phosphate buffer, pH 7.0, containing 5 mM EDTA at 30° C. for 30 minutes.

6. Preparation of maleimide-dinitrophenyl-biotinyl-nonspecific rabbit IgG

The maleimide-dinitrophenyl-nonspecific rabbit IgG (2.0 mg) in 0.1M sodium phosphate buffer, pH 6.0 (3.2 ml) containing 5 mM EDTA was incubated with 0.11 ml of N-biotinyl-2-mercaptoethylamine at 30° C. for 30 minutes. After incubation, the reaction mixture was subjected to gel filtration on a column (1.0×30 cm) of Sephadex G-25 using 0.1M sodium phosphate buffer, pH 6.0, containing 5 mM EDTA. The average number of biotinyl groups introduced per maleimide-dinitrophenyl-nonspecific rabbit IgG molecule was 14.4 as calculated from the decrease in the number of maleimide groups in maleimide-dinitrophenyl-nonspecific rabbit IgG.

7. Preparation of dinitrophenyl-biotinyl-nonspecific rabbit IgG-rabbit anti-thyroglobulin Fab' conjugate The maleimide-dinitrophenyl-biotinyl-nonspecific rabbit IgG (1.3 mg) in 0.1M sodium phosphate buffer, pH 6.0 (0.1 ml), containing 5 mM EDTA was incubated with 0.1 ml of rabbit anti-thyroglobulin Fab' (0.4 mg) in the same buffer at 4° C. for 20 hours. After incubation, the reaction mixture was subjected to gel filtration on a column (1.5×45 cm) of Ultrogel AcA 22 using 0.1M sodium phosphate buffer, pH 7.0, containing 0.1% NaN$_3$. The average number of rabbit anti-thyroglobulin Fab' fragments introduced per dinitrophenyl-biotinyl-nonspecific rabbit IgG molecule was 0.8.

8. Preparation of dinitrophenyl-biotinyl-nonspecific rabbit IgG-affinity-purified rabbit anti-thyroglobulin Fab' conjugate Dinitrophenyl-biotinyl-nonspecific rabbit IgG-rabbit anti-thyroglobulin Fab' (0.5 mg) in 0.1M sodium phosphate buffer, pH 7.0 (0.5 ml), containing 0.1% NaN$_3$ was passed through a column (3.5×2.6 mm) of thyroglobulin-coated Sepharose 4B equilibrated with the same buffer, after which it was eluted with 3.2 mM hydrochloric acid, pH 2.5, to give dinitrophenyl-biotinyl-rabbit nonspecific IgG-affinity-purified rabbit anti-thyroglobulin Fab' (0.06 mg).

Preparation of avidin-biotinyl-nonspecific rabbit IgG-coated polystyrene ball

Biotinyl-nonspecific rabbit IgG (0.1 g/l) was physically adsorbed to a polystyrene ball in the same manner as in Example 1, whereafter the biotinyl-nonspecific IgG-coated polystyrene ball was incubated with 0.1M sodium phosphate buffer, pH 7.0, containing 0.1% avidin and 0.1% NaN$_3$ at 37° C. for 4 hours.

Assay of anti-thyroglobulin antibody

Figure 5:
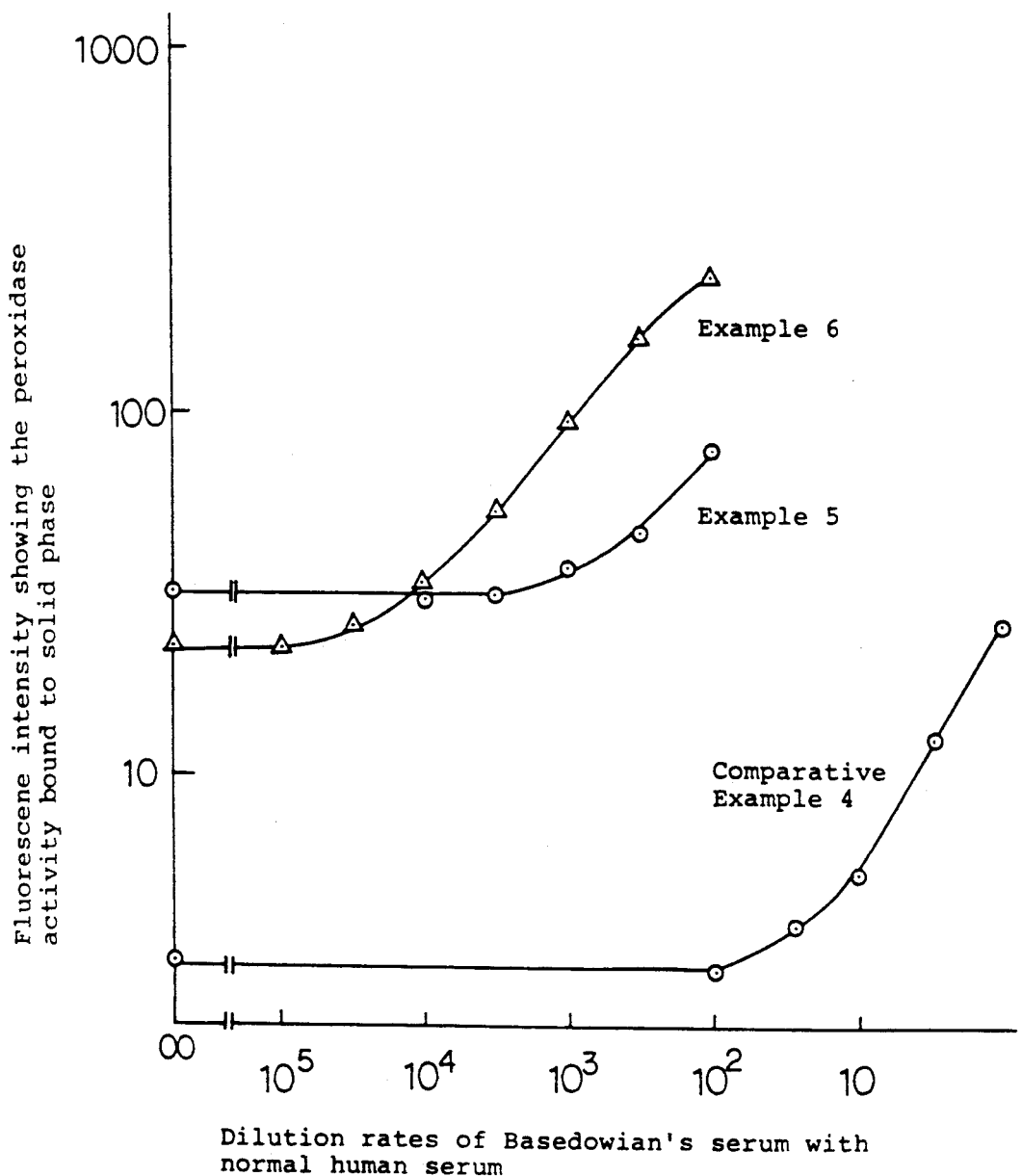

An aliquot (0.02 ml) of sample prepared by diluting human serum containing anti-thyroglobulin antibody with normal human serum at various dilution rates was incubated with 0.06 ml of 0.01M sodium phosphate buffer, pH 7.0, containing 30 fmol of thyroglobulin, 0.1M NaCl and 0.1% bovine serum albumin, and 0.05 ml of 0.01M sodium phosphate buffer, pH 7.0, containing 1M NaCl and 0.1% bovine serum albumin at 37° C. for 4 hours. This reaction mixture was further incubated with 100 fmol of dinitrophenyl-biotinyl-nonspecific rabbit IgG-affinity-purified rabbit (anti-thyroglobulin) Fab' conjugate in 0.01 ml of 0.01M sodium phosphate buffer, pH 7.0, containing 0.1M NaCl and 0.1% bovine serum albumin at 37° C. for 4 hours, and 4° C. overnight. To the mixture, 0.01 ml of 0.01M sodium phosphate buffer, pH 7.0, containing 3% nonspecific rabbit IgG, 0.1M NaCl and 0.1% bovine serum albumin was added, and the mixture was incubated with affinity-purified rabbit (anti-dinitrophenylbovine serum albumin) IgG-coated polystyrene ball at 24° C. for 4 hours. After incubation, the polystyrene ball was washed twice with 2 ml of 0.01M sodium phosphate buffer, pH 7.0, containing 0.1M NaCl and incubated with 150 nmol of dinitrophenyl-L-lysine in 0.15 ml of 0.01M sodium phosphate buffer, pH 7.0, containing 0.2% nonspecific rabbit IgG, 0.1M NaCl and 0.1% bovine serum albumin, at room temperature overnight. After removal of the polystyrene ball, the eluate was incubated with an avidin-biotinyl-nonspecific rabbit IgG-coated polystyrene ball at 20° C. for 3 hours. After incubation, the polystyrene ball was washed twice with 2 ml of 0.01M sodium phosphate buffer, pH 7.0, containing 0.1M NaCl, and incubated with rabbit (anti-human IgG γ-chain) Fab'-peroxidase (50 ng) in 0.15 ml of 0.01M sodium phosphate buffer, pH 7.0, containing 0.1M NaCl and 0.1% bovine serum albumin at 20° C. for 3 hours. After washing the polystyrene ball in the same manner as above, peroxidase activity bound to the polystyrene ball was assayed at 30° C. for 10 minutes. As shown in FIG. 5, assay was possible up to $10^3$-fold dilution.

EXAMPLE 6

Assay of peroxidase activity, preparation of IgG-coated solid phase and pretreatment of IgG-coated solid phase were conducted in accordance with the methods of Example 2. Preparation of protein-Sepharose 4B and affinity-purification of IgG were conducted in accordance with the methods of Example 3. Purification of thyroglobulin was conducted in accordance with the method of Example 4.

Preparation of dinitrophenyl-thyroglobulin-peroxidase conjugate

1. Preparation of mercaptosuccinylated-thyroglobulin

The thyroglobulin (1.4 mg) in 2.8 ml of 0.1M sodium phosphate buffer, pH 7.5 was incubated with 0.25 ml of 55 mM S-acetylmercaptosuccinic anhydride (Nakarai Chemicals, Kyoto, Japan) in N,N-dimethylformamide at 30° C. for 30 minutes. After incubation, the reaction mixture was subjected to gel filtration on a column of Sephadex G-25 (1.0×30 cm) using 0.1 sodium phosphate buffer, pH 7.0, containing 5 mM EDTA. The fraction (4.0 ml) containing 1.2 mg of S-acetylmercaptosuccinyl-thyroglobulin was incubated with 0.4 ml of 1.0M hydroxylamine, pH 7.0 at 30° C. for 15 minutes, and subjected to gel filtration on a column (1.0×30 cm) of Sephadex G-25 using 0.1M sodium phosphate buffer, pH 6.0, containing 5 mM EDTA. The average number of thiol groups introduced per thyroglobulin molecule was 22.

2. Preparation of maleimide-dinitrophenyl-L-lysine

The procedure of Example 5 was followed.

3. Preparation of mercaptosuccinylated dinitrophenylthyroglobulin

An aliquot (0.5 ml) of the maleimide-dinitrophenyl-L-lysine solution was incubated with mercaptosuccinylated thyroglobulin (1.05 mg) in 0.1M sodium phosphate buffer, pH 6.0 (0.5 ml), containing 5 mM EDTA at 30° C. for 30 minutes. After incubation, the mixture was subjected to gel filtration on a column (1.5×30 cm) of Sephadex G-25 using the same buffer. The average number of dinitrophenyl groups introduced per mercaptosuccinylated thyroglobulin molecule was 11.

4. Preparation of dinitrophenyl-thyroglobulin-peroxidase

The mercaptosuccinylated dinitrophenyl-thyroglobulin (0.6 mg) in 0.1M sodium phosphate buffer, pH 6.0 (0.3 ml), containing 5 mM EDTA was incubated with the maleimide-peroxidase (1.0 mg) prepared in Example 3 in the same buffer (0.03 ml) at 4° C. for 20 hours, and the reaction mixture was incubated with 5 μl of 0.1M N-ethylmaleimide in the same buffer at 30° C. for 15 minutes. After incubation, the reaction mixture was subjected to gel filtration on a column (1.5×45 cm) of Ultrogel AcA 22 using 0.1M sodium phosphate buffer, pH 6.5. The average number of peroxidase molecules introduced per dinitrophenyl-thyroglobulin molecule was 1.4.

Assay of anti-thyroglobulin antibody

An aliquot (0.01 ml) of sample prepared by diluting human serum containing anti-thyroglobulin antibody with normal human serum at various dilution rates was incubated with 0.09 ml of 0.01M sodium phosphate buffer, pH 7.0, containing 15 fmol of dinitrophenyl-thyroglobulin-peroxidase conjugate, 0.333% nonspecific rabbit IgG, 0.1% bovine serum albumin and 0.1M NaCl, 0.05 ml of 0.01M sodium phosphate buffer, pH 7.0, containing 1.0M NaCl and 0.1% bovine serum albumin, and two affinity-purified rabbit (anti-dinitrophenyl-bovine serum albumin) IgG-coated polystyrene balls at 20° C. for 3 hours. After incubation, the polystyrene balls were washed twice with 2 ml of 0.01M sodium phosphate buffer, pH 7.0, containing 0.1M NaCl and incubated with 150 nmol of dinitrophenyl-L-lysine in 0.15 ml of 0.01M sodium phosphate buffer, pH 7.0, containing 0.1M NaCl and 0.1% bovine serum albumin, and two affinity-purified rabbit (anti-human IgG γ-chain) IgG-coated polystyrene balls at 20° C. for 3 hours. After washing the affinity-purified rabbit (anti-human IgG γ-chain) IgG-coated polystyrene balls in the same manner as above, peroxidase activity bound to the polystyrene balls was assayed at 30° C. for 10 minutes. As shown in FIG. 5, assay was possible up to $5 \times 10^4$-fold dilution.

Assay of anti-thyroglobulin antibody was achieved with higher sensitivity in Examples 4, 5 and 6 according to the method of the present invention, as compared with Comparative Example 4 according to the conventional method.

EXAMPLE 7

Preparation of IgG, and preparations of affinity-purified rabbit (anti-dinitrophenyl-bovine serum albumin) IgG-coated solid phase and of affinity-purified rabbit (anti-human IgG γ-chain) IgG coated solid phase were conducted in accordance with the methods of Example 2. Assay of peroxidase activity was conducted in accordance with the methods of Example 2 using 0.2 mg/l of quinine in 50 mM sulfuric acid as standard. Affinity purification of IgG and preparation of rabbit (anti-human IgG γ-chain) IgG-Sepharose 4B were conducted in accordance with the methods of Example 3. Purification of thyroglobulin and preparation of dinitrophenyl-thyroglobulin were conducted in accordance with the methods of Example 4.

Preparation of thyroglobulin-peroxidase

1. Preparation of mercaptosuccinylated thyroglobulin

Thiol groups were introduced into purified thyroglobulin by a known method using S-acetylmercaptosuccinic anhydride [Ishikawa et al., Journal of Immunoassay (mentioned above)]. The average number of thiol groups introduced per thyroglobulin molecule was 3.8.

2. Preparation of maleimide-peroxidase

Maleimide groups were introduced into horseradish peroxidase by a known method using N-succinimidyl-6-maleimidohexanoate [Hashida et al., Journal of Applied Biochemistry (mentioned above)]. The average number of maleimide groups introduced per peroxidase molecule was 1.3.

3. Preparation of thyroglobulin-peroxidase

Mercaptosuccinylated thyroglobulin (0.31 mg) in 0.07 ml of 0.1M sodium phosphate buffer, pH 6.0, containing 5 mM EDTA was incubated with 93 μg of maleimide-peroxidase in 0.005 ml of 0.1M sodium phosphate buffer, pH 6.0, containing 5 mM EDTA at 4° C. for 20 hours. The reaction mixture was subjected to gel filtration on a column (1.5×45 cm) of Ultrogel AcA 22 (LKB, Stockholm, Sweden) using 0.1M sodium phosphate buffer, pH 6.5. The average number of peroxidase groups introduced per thyroglobulin molecule was 1.7.

Purification of human anti-thyroglobulin IgG

The serum sample was collected from patients with Basedow's disease and IgG in the serum of the patients was purified by fractionation with sodium sulfate followed by passage through a column of DEAE cellulose. IgG (4 mg) thus obtained was dissolved in 0.5 ml of 0.1M sodium phosphate buffer, pH 7.0, containing 0.1% NaN$_3$.

Affinity-purification was conducted by a known method of eluting at pH 2.5 using thyroglobulin-Sepharose 4B column (1×3 mm) [Kohno et al., Journal of Biochemistry 100, 1247 (1986)] in accordance with the methods of Example 3 to give human anti-thyroglobulin IgG (5.1 μg).

Assay of anti-thyroglobulin antibody

An aliquot (0.02 ml) of sample prepared by diluting human anti-thyroglobulin IgG with normal human serum at various concentration rates was incubated with 100 fmol of dinitrophenyl-thyroglobulin, 100 fmol of thyroglobulin-peroxidase conjugate in 0.13 ml of 0.01M sodium phosphate buffer, pH 7.0, containing 0.46M NaCl and 0.1% bovine serum albumin, at 20° C. for 3 hours. After incubation, the reaction mixture was incubated with two affinity-purified rabbit (anti-dinitrophenyl-bovine serum albumin) IgG-coated polystyrene balls at 20° C. for 3 hours and 4° C. overnight. After incubation, the polystyrene balls were washed twice with 2 ml of 0.01M sodium phosphate buffer, pH 7.0, containing 0.1M NaCl, and incubated with 150 nmol of dinitrophenyl-L-lysine in 0.15 ml of 0.01M sodium phosphate buffer, pH 7.0, containing 0.1M NaCl and 0.1% bovine serum albumin, and two affinity-purified rabbit (anti-human IgG γ-chain) IgG-coated polystyrene balls at 20° C. for 1 hour. After removal of two affinity-purified rabbit (anti-dinitrophenyl-bovine serum albumin) IgG-coated polystyrene balls, the eluate and affinity-purified rabbit (anti-human IgG γ-chain) IgG-coated polystyrene balls were further incubated at 20° C. for 2 hours, then washed in the same manner as above, and the peroxidase activity bound to the polystyrene balls was assayed at 30° C. for 150 minutes. The results are shown in FIG. 6.

COMPARATIVE EXAMPLE 5

Human anti-thyroglobulin IgG was assayed in the same manner as in Comparative Example 4 using a sample prepared by diluting a known amount of human anti-thyroglobulin IgG with normal human serum at various concentration rates. The results are shown in FIG. 6.

EXAMPLE 8

Buffer

The regularly used buffer was 0.01M sodium phosphate buffer, pH 7.0, containing 0.1M NaCl, 1 mM $MgCl_2$, 0.1% bovine serum albumin and 0.1% $NaN_3$, (buffer A).

Standard sample of hTSH

A preparation included in the hTSH kit "Daiichi" (Daiichi Radioisotope Labs., Tokyo, Japan) was used as a standard sample of hTSH.

Preparation of IgG, F(ab')$_2$, and Fab'

IgG, F(ab')$_2$ and Fab' were prepared by fractionation with sodium sulfate followed by passage through a column of DEAE cellulose, by digestion of IgG with pepsin and by reduction of F(ab')$_2$, respectively, by a known method [Ishikawa et al., Journal of Immunoassay (mentioned above)].

Preparation of dinitrophenyl-monoclonal mouse (anti-hTSH β-subunit) IgG$_1$

1. Preparation of mercaptosuccinylated monoclonal mouse (anti-hTSH β-subunit) IgG$_1$ Thiol groups were introduced into monoclonal mouse (anti-hTSH β-subunit) IgG$_1$ (Mallinckrodt, Inc., St. Louis, Mo.) by a known method using S-acetylmercaptosuccinic anhydride, [Ishikawa et al., Journal of Immunoassay (mentioned above)]. The average number of thiol groups introduced per monoclonal mouse (anti-hTSH β-subunit) IgG$_1$ molecule was 10.5.

2. Preparation of maleimide-dinitrophenol-L-lysine

An aliquot (0.9 ml) of 5.5 mM dinitrophenyl-L-lysine in 0.1M sodium phosphate buffer, pH 7.0, containing 5 mM EDTA, and 0.10 ml of 5 mM N-succinimidyl-6-maleimidohexanoate (mentioned above) in N,N-dimethylformamide at 30° C. for 30 minutes.

3. Preparation of dinitrophenyl-monoclonal mouse (anti-hTSH β-subunit) IgG$_1$

An aliquot (0.5 ml) of maleimide-dinitrophenyl-L-lysine solution was incubated with 0.1 mg of mercaptosuccinylated monoclonal mouse (anti-hTSH β-subunit) IgG$_1$ in 4.5 ml of 0.1M sodium phosphate buffer, pH 6.0, containing 5 mM EDTA at 30° C. for 30 minutes. The reaction mixture was subjected to gel filtration on a column (1.0×30 cm) of Sephadex G-25 using 0.1M sodium phosphate buffer, pH 7.0. The average number of dinitrophenyl groups introduced per monoclonal mouse (anti-hTSH β-subunit) IgG$_1$ molecule was 7.2.

Preparation of dinitrophenyl-bovine serum albumin

Dinitrophenyl-bovine serum albumin was prepared in the same manner as above, using bovine serum albumin (fraction V, Armour Pharmaceutical Co., Kankakee, Ill.).

The average number of dinitrophenyl groups introduced per bovine serum albumin molecule was 7.0.

Preparation of protein-Sepharose 4B

According to the instructions of Pharmacia, hCG (2.5 mg), dinitrophenyl-bovine serum albumin (10 mg) and nonspecific mouse IgG (20 mg) were bound to CNBr-activated Sepharose 4B (1 g).

Affinity-purification of IgG

Rabbit (anti-hCG) F(ab')$_2$ prepared from rabbit (anti-hCG) IgG (Dakopatts a/s, Glostrup, Denmark), rabbit (anti-dinitrophenyl-bovine serum albumin) IgG (Miles Co., Elkhart, Ind.) and rabbit (anti-mouse IgG) IgG (Medical and Biological Laboratories, Nagoya, Japan) were affinity-purified by elution at pH 2.5 from columns of hCG, dinitrophenyl-bovine serum albumin and nonspecific mouse IgG-coupled Sepharose 4B, respectively, by a known method [Kohno et al., Journal of Biochemistry, 100, 1247 (1986)].

Assay of β-D-galactosidase activity

β-D-galactosidase activity was assayed fluorometrically by a known method [Imagawa et al., Annals Clinical Biochemistry, 21, 310 (1984)] using 4-methylumbelliferyl β-D-galactoside as substrate after 16 hours of reaction at 30° C. Fluoroscene intensity was measured relative to $10^{-8}$M 4-methylumbelliferone in 0.1M glycine-NaOH buffer, pH 10.3.

Preparation of affinity-purified rabbit anti-(hCG) Fab'-β-D-galactosidase

Affinity-purified rabbit anti(hCG) Fab' was conjugated with β-D-galactosidase by a known method [Ishikawa et al., Scandinavian Journal of Immunology, 8 (supple. 7), 43 (1978)] using N,N'-o-phenylenedimaleimide as cross linking agent. The average number of Fab' molecules conjugated per β-D-galactosidase molecule was 2.1.

Fab'-β-D-galactosidase conjugates (0.8 mg) in 0.5 ml of buffer A were passed through a column (0.55×1.0 cm) of nonspecific mouse serum protein-Sepharose 4B using buffer A. The amount of conjugate was calculated from enzyme activity.

Preparation of affinity-purified rabbit (anti-dinitrophenyl-bovine serum albumin) IgG and affinity-purified rabbit (anti-mouse IgG) IgG-coated solid phase Polystyrene balls (3.2 mm in diameter; Precision Plastic Ball Co., Chicago, Ill.) were coated by physical adsorption with affinity-purified rabbit (anti-dinitrophenyl-bovine serum albumin) IgG solution (0.1 g/l) or affinity-purified rabbit (anti-mouse IgG) IgG solution (0.1 g/l) by a known method [Ishikawa et al., Scandinavian Journal of Immunology (mentioned above)].

Assay of hTSH

Affinity-purified rabbit anti-(hCG) Fab'-β-D-galactosidase (200 fmol) in 0.01 ml of buffer A was incubated with 200 fmol of 0.1 µg of nonspecific mouse IgG in 0.01 ml of buffer A at 20° C. for 2 hours.

Dinitrophenyl-monoclonal mouse (anti-hTSH β-subunit) IgG$_1$ (150 fmol) in 0.02 ml of buffer A was incubated with 0.1 mg of nonspecific rabbit F(ab')$_2$ in 0.02 ml of buffer A at 20° C. for 2 hours.

These two incubation mixtures were then mixed together and incubated with various concentrations of hTSH standard samples in solution in 0.09 ml of buffer A at 20° C. overnight. To the reaction mixture, two affinity-purified rabbit (anti-dinitrophenyl-bovine serum albumin) IgG-coated polystyrene balls were added, and incubation was continued at 20° C. for 4 hours.

After removal of the incubation mixture, the polystyrene balls were washed twice with 2 ml of buffer A and incubated with 0.15 ml of buffer A containing 1 mM of dinitrophenyl-L-lysine and 0.1 mg of nonspecific rabbit F(ab')$_2$ and two affinity-purified rabbit (anti-mouse IgG) IgG-coated polystyrene balls at 20° C. for 4 hours.

After washing the affinity-purified rabbit (anti-mouse IgG) IgG-coated polystyrene balls in the same manner as above, $\beta$-D-galactosidase activity bound to the polystyrene balls was assayed at 30° C. for 16 hours. The results are shown in FIG. 7, along with the results in Comparative Example 6 below. FIG. 7 is a graph showing the results of assay by the method of the present invention and by the conventional method, as expressed in the relationship between hTSH concentration (nU/tube, abscissa) and fluorescene intensity corresponding to specifically bound $\beta$-D-galactosidase (ordinate).

COMPARATIVE EXAMPLE 6

The buffer and hTSH standard sample were the same as those in Example 8. Assay of $\beta$-D-galactosidase activity, preparation of affinity-purified rabbit (anti-hCG) Fab'-$\beta$-D-galactosidase, and preparation of monoclonal mouse (anti-hTSH $\beta$-subunit) IgG$_1$-coated polystyrene balls were conducted in the same manner as in Example 8.

Assay of hTSH

A monoclonal mouse anti-(hTSH $\beta$-subunit) IgG$_1$-coated polystyrene ball was incubated with standard sample of hTSH in 0.15 ml of buffer A at 20° C. overnight.

After removal of the incubation mixture, the polystyrene ball was washed twice with 2 ml of buffer A, and incubated with 200 fmol of affinity-purified rabbit (anti-hCG) Fab'-$\beta$-D-galactosidase and 0.1 mg of nonspecific rabbit F(ab')$_2$ in at 20° C. for 4 hours.

After washing the polystyrene ball in the same manner as above, $\beta$-D-galactosidase activity bound to the polystyrene ball was assayed at 30° C. for 1 hour. The results are shown in FIG. 7.

EXAMPLE 9

The buffer was the same as the one used in Example 8. Preparation of IgG, F(ab')$_2$ and Fab', preparation of protein-Sepharose 4B, affinity-purification of IgG and preparation of affinity-purified (anti-dinitrophenyl-bovine serum albumin) IgG-coated solid phase and affinity-purified rabbit (anti-mouse IgG) IgG-coated solid phase were conducted in accordance with the methods of Example 8.

Standard sample of hGH

A preparation included in an hGH RIA kit (Dainabot Co., Ltd., Tokyo, Japan) was used as standard sample of hGH. Preparation of dinitrophenyl-monoclonal mouse (anti-hGH) IgG$_1$.

The procedure of Example 8 was followed. The number of dinitrophenyl groups introduced per monoclonal mouse (anti-hGH) IgG$_1$ molecule was 5.7.

Preparation of rabbit (anti-hGH) Fab'-$\beta$-D-galactosidase conjugate

The procedure of Example 8 was followed. The average number of Fab' molecules conjugated per $\beta$-D-galactosidase molecule was 4.1.

Assay of hGH

Affinity purified rabbit anti-(hGH) Fab'-$\beta$-D-galactosidase conjugate (200 fmol) in 0.01 ml of buffer A was incubated with 0.1 $\mu$g of nonspecific mouse IgG in 0.01 ml of buffer A at 20° C. for 2 hours.

Dinitrophenyl-monoclonal mouse (anti-hGH) IgG$_1$ (150 fmol) in 0.02 ml of buffer A was incubated with 0.1 mg of nonspecific rabbit F(ab')$_2$ in 0.02 ml of buffer A at 20° C. for 2 hours.

These two incubation mixtures were then mixed together and incubated with various concentrations of standard sample of hGH in 0.09 ml of buffer A at 20° C. overnight. To the reaction mixture, two affinity-purified rabbit (anti-dinitro-phenyl-bovine serum albumin) IgG-coated polystyrene balls were added, and incubation was continued at 20° C. for 4 hours.

After removal of the incubation mixture, polystyrene balls were washed twice with 2 ml of buffer A and incubated with 0.15 ml of buffer A containing 1 mM dinitrophenyl-L-lysine and 0.1 mg of nonspecific rabbit F(ab')$_2$, and two affinity-purified rabbit (anti-mouse IgG) IgG-coated polystyrene balls at 20° C. for 4 hours.

After washing the affinity-purified rabbit (anti-mouse IgG) IgG-coated polystyrene balls in the same manner as above, $\beta$-D-galactosidase activity bound to the polystyrene ball was assayed at 30° C. for 16 hours. The results are shown in FIG. 8, along with the results in Comparative Example 7 below. FIG. 8 is a graph showing the results of assay by the method of the present invention and by the conventional method, as expressed in the relationship between hGH concentration (pg/tube, abscissa) and fluorescene intensity corresponding to specifically bound $\beta$-D-galactosidase (ordinate).

COMPARATIVE EXAMPLE 7

The buffer was the same as the one in Example 8. Assay of $\beta$-D-galactosidase activity and preparation of monoclonal mouse (anti-hGH) IgG-coated solid phase were conducted in the same manner as in Example 9.

Assay of hGH

A monoclonal mouse (anti-hGH) IgG$_1$-coated polystyrene ball was incubated with standard sample of hGH in 0.15 ml of buffer A at 20° C. overnight.

After removal of the incubation mixture, the polystyrene ball was washed twice with 2 ml of buffer A, and incubated with 200 fmol of rabbit (anti-hGH) Fab'-D-galactosidase and 0.1 mg of nonspecific rabbit F(ab')$_2$ in 0.15 ml of buffer A at 20° C. for 4 hours.

After washing the polystyrene ball in the same manner as above, $\beta$-D-galactosidase activity bound to the polystyrene ball was assayed at 30° C. for 1 hour. The results are shown in FIG. 8.

EXAMPLE 10

Assay of peroxidase activity, preparation of IgG-coated solid phase and preparation of rabbit (anti-thyroglobulin) Fab'-peroxidase were conducted in accordance with the methods of Example 2. Affinity purification of IgG was conducted with the methods of Example 3. Purification of thyroglobulin and preparation of dinitrophenyl-thyroglobulin were conducted with the methods of Example 4.

Assay of anti-thyroglobulin antibody

An aliquot (0.02 ml) of sample prepared by diluting human serum containing anti-thyroglobulin antibody with normal human serum at various dilution rates was incubated with 0.08 ml of 0.01M sodium phosphate, pH 7.0, containing 15 fmol of dinitrophenyl thyroglobulin, 3.75 g/l nonspecific rabbit IgG 1 g/l $NaN_3$, 0.1M NaCl and 0.1% bovine serum albumin, 0.05 ml of 0.01M sodium phosphate buffer, pH 7.0, containing 0.1M NaCl, 0.1% bovine serum albumin and 0.1% $NaN_3$ and two affinity-purified rabbit (anti-dinitrophenyl bovine serum albumin) IgG-coated polystyrene balls at 20° C. for 4 hours and at 4° C. overnight. The polystyrene balls had been treated with nonspecific rabbit IgG as described in Example 2. After incubation, the polystyrene balls were washed twice with 2 ml of 0.01M sodium phosphate buffer, pH 7.0, containing 0.1M NaCl and incubated with 150 nmol dinitrophenyl-L-lysine in 0.15 ml of 0.01M sodium phosphate buffer containing 0.1% $NaN_3$, 0.1M NaCl and 0.1% bovine serum albumin at 20° C. for 1 hour to elute the complex of anti-thyroglobulin IgG and dinitrophenyl thyroglobulin. After removal of the polystyrene balls, the eluate was incubated with an affinity-purified rabbit (anti-human IgG γ-chain) IgG-coated polystyrene ball at 20° C. for 3 hours. After incubation, the rabbit (anti-human IgG γ-chain) IgG-coated polystyrene ball was washed as described above, and incubated with rabbit anti-thyroglobulin Fab'-peroxidase conjugate (50 ng) in 0.15 ml of 0.01M sodium phosphate buffer, pH 7.0, containing 0.1M NaCl and 0.1% bovine serum albumin at 20° C. for 3 hours.

Finally, the polystyrene ball was washed as described above and peroxidase activity bound to the polystyrene ball was assayed at 30° C. for 10 minutes. Assay was possible up to $10^5$-fold dilution.

The method of Example 10 according to the present invention permits assay of anti-thyroglobulin antibody with higher sensitivity as compared with the conventional methods of Comparative Example 4.

What is claimed is:

1. A method of high sensitivity immunoassay for assaying an object substance, which is an antigenic substance or a specific antibody to be assayed, in a test solution, the method comprising the following steps:
  A) adding to the test solution
    1) at least one active component conjugated with at least one functional group; the active component being one which is capable of binding with the object substance, and the functional group being one which is capable of binding to a reactive group on a solid carrier; and also adding
    2) at least one solid carrier, the first carrier, with at least one reactive group which is capable of binding with said functional group;
    to form a complex, composed of the object substance and the active component, bound to said first carrier;
  B) dissociating the complex from the solid carrier;
  C) adding a second solid carrier, having a reactive group capable of binding with the complex, to the complex dissociated in step (B) to form a complex bound to said second solid carrier; and
  D) assaying for the complex, bound to the second solid carrier.

2. A method of claim 1 wherein the object substance is an antigenic substance.

3. A method of claim 1 wherein the object substance is a specific antibody.

4. A method of claim 1 wherein step (B) comprises adding to the complex bound to the first carrier a sufficient amount of a substance having the same functional group as that of the active component to effect dissociation of the complex from the carrier.

5. A method of claim 1 wherein the active component conjugated with at least one functional group is bound thereto through an S—S bond.

6. A method of claim 5 wherein step (B) comprises adding to the complex bound to the first carrier a sufficient amount of a reagent capable of breaking the S—S bond.

7. A method of high sensitivity immunoassay as claimed in claim 1, wherein at least one active component is labeled with a marker.

8. A method of high sensitivity immunoassay as claimed in claim 1, wherein the complex, comprising the active component and the specific antibody or antigenic substance to be assayed, is formed in a test solution, and subsequently bound with the solid carrier in (A).

9. A method of immunoassay as claimed in claim 3 wherein an antigen as active component, prebound with two kinds of functional groups, is bound to a solid carrier by one of the two functional groups in (A), the active component is bound to another solid carrier by the other functional group in (C), and the antibody in the complex on the carrier is assayed by a labeled anti-antibody in (D).

10. A method of immunoassay as claimed in claim 3 wherein an antigen as active component, pre-bound with a functional group and a marker, is bound to a solid carrier by the functional group in (A), an anti-antibody-bound carrier is used in (C), and the market in the complex on the carrier is assayed in (D).

11. A method of immunoassay as claimed in claim 3 in which some antibodies are in the form of an antigen-antibody complex in the test solution, wherein an antigen and an antibody are active components, free antibodies are bound with an added antigen to form an antigen-antibody complex, a functional group-bound and labeled antibody is added to form an antibody-antigen-antibody complex, the complex thus obtained is bound to a solid carrier by the functional group in (A), a solid carrier bound with an anti-antibody against the antibody to be assayed is used in (C), and a marker in the complex on the solid carrier is assayed in (D).

12. A method of immunoassay as claimed in claim 9 wherein the anti-antibody is capable of immunoglobulin class recognition.

13. A method of immunoassay as claimed in claim 2 wherein two different antibodies derived from two animal species are active components, one being bound with a functional group, and the other being bound with a marker, are coupled together to form a complex, the complex thus obtained is bound to a solid carrier by the functional group in (A), a solid carrier bound with an anti-antibody against the functional group-bound antibody is used in (C), and the marker in the complex on the solid carrier is assayed in (D).

14. A method of immunoassay as claimed in claim 2 wherein two kinds of antibodies derived from the same animal species are active components, one being bound with two kinds of functional groups, and the other being bound with a marker, are bound together to form a complex, the complex thus obtained is bound to a solid carrier by one of the two functional groups in (A), another solid carrier capable of binding with the other functional group is used in (C), and the marker in the complex on the solid carrier is assayed in (D).

15. A method of immunoassay as claimed in claim 10 and wherein the anti-antibody in capable of immunoglobulin class recognition.

16. A method of immunoassay as claimed in claim 11 and wherein the anti-antibody is capable of immunoglobulin class recognition.

17. A method of immunoassay as claimed in claim 1 wherein the complex and the solid carrier are bound in each of (A) and (C) via a reactive group, and the reactive group bound to the solid carrier in (C) is different from the reactive group in (A).

18. A method of immunoassay as claimed in claim 2 wherein an antigen and an antibody are active components, the antigen labeled with a marker, and the antibody, bound to a functional group, are bound together to form a complex, the resulting complex is bound to a solid carrier which is bound to an anti-antibody against the antibody, the thus-obtained solid carrier is that used in (C), and the marker in the complex on the solid carrier is assayed in (D).

19. A method of high sensitivity immunoassay as claimed in claim 1, wherein the active component is (i) an antigen or antibody causing an antigen-antibody reaction with the specific antibody or antigenic substance to be assayed or (ii) an antigen or antibody causing an antigen-antibody reaction with the antigen or antibody in (i).

20. A method of high sensitivity immunoassay as claimed in claim 1, wherein the functional group is (i) a hapten or hapten bound via an —S—S— linkage, (ii) biotin or biotin bound via an —S—S— linkage or (iii) an antibody or antigen, other that the specific antibody or antigenic substance to be assayed, bound via an —S—S— linkage.

21. A method of high sensitivity immunoassay as claimed in claim 1, wherein the reactive group is (i) an anti-hapten antibody, when the functional group is a hapten, (ii) avidin or streptoavidin, when the functional group is biotin, or (iii) an antigen or antibody corresponding to the functional group, when the functional group is an antibody or antigen, other than the specific antibody or antigenic substance to be assayed, bound via an —S—S— linkage.

22. A method of high sensitivity immunoassay as claimed in claim 1, wherein the active component is bound with at least two functional groups.

* * * * *